United States Patent [19]
Okumura

[11] Patent Number: 5,926,251
[45] Date of Patent: Jul. 20, 1999

[54] EYE IMAGE TRACKING APPARATUS

[75] Inventor: Tomoko Okumura, Tokyo, Japan

[73] Assignee: Mitsubishi Denki Kabushiki Kaisha, Tokyo, Japan

[21] Appl. No.: 09/002,350

[22] Filed: Jan. 2, 1998

[30]     Foreign Application Priority Data

Aug. 12, 1997   [JP]   Japan ................................. 9-217709

[51] Int. Cl.⁶ ...................................................... A61B 3/14
[52] U.S. Cl. ........................................................ 351/209
[58] Field of Search ................................. 351/209, 210, 351/206, 211, 246; 382/115, 117, 173, 286

[56]              References Cited

U.S. PATENT DOCUMENTS

| 4,856,891 | 8/1989 | Pflibsen et al. | 351/210 |
| 5,016,282 | 5/1991 | Tomono et al. | 382/117 |
| 5,818,954 | 10/1998 | Tomono et al. | 382/115 |

FOREIGN PATENT DOCUMENTS 6-32154   2/1994   Japan .

*Primary Examiner*—George Manuel
*Attorney, Agent, or Firm*—Sughrue, Mion, Zinn, Macpeak & Seas, PLLC

[57]              ABSTRACT

The present invention provides an eye image tracking apparatus capable of tracking not only images of the eyes but also images of their periphery to accurately track the images of the eyes without erroneous detection while recognizing missing of the eyes when the eyes have been missed. The eye image tracking apparatus comprises a face image input portion 4 for inputting an image of a face, a digitalizing portion 5 for digitalizing the input image of the face, an image retrieval portion 6 for retrieving images of the eyes and their periphery within the digitalized image, and an image tracking portion 7 for tracking the retrieved images of the eyes and their periphery.

7 Claims, 22 Drawing Sheets

DUPLICATE PATTERN 1

DUPLICATE PATTERN 2

"13up" IS BEING TRACKED.

"13eye" IS BEING TRACKED.

"13dwn" IS BEING TRACKED.

(a) PREVIPUS SCREEN (b) CURRENT SCREEN

EYE IMAGE TRACKING APPARATUS

BACKGROUND OF THE INVENTION

1. Field of the Invention

The present invention relates to an eye image tracking apparatus that can track images of the eyes more accurately by using image processing to retrieve and track images around the eyes as well as those of eyes themselves.

2. Description of the Related Art

A conventional eye image tracking apparatus for a driver of a vehicle is described, for example, in Japanese Patent Application Laid-Open No. 6-32154. The overall configuration of this apparatus comprises an image input means 51, a digitalizing means 52, an eyeball-existing-region setting means 53, an eyeball detection means 54, an eye-state detection means 55, and a driver condition determination means 56, as shown in a block diagram in FIG. 22.

The main flow of the operation of this apparatus is shown in FIG. 23. After the system has been activated, a timer is started at step S1. At step S2, the driver's face is photographed, and this image is converted into a digital signal, which is then stored in an image memory as input image data for a single frame at step S3. The input image data stored in the image memory is digitalized at step S4 to determine the horizontal and vertical widths of the first (i.e., right) and second (i.e., left) eyeball-existing-regions at step S5 and step S6. Then, the eyeballs are detected at step 7, and an eye state (i.e., opened or closed eye) is determined at step S8. The count of the timer having been started at step S1 is used in this step. The eyeball detection means 54 scans all the vertical pixels in each of the right and left eyeball-existing regions for each horizontal dot to retrieve the number of continuous black pixels in order to detect the eyeballs. Finally, it is determined whether or not the driver is dozing at step S9. After this series of processing, the process returns to step S2 to repeat this processing.

The regions in the image that are digitalized, however, are unstable due to the influences of the presence of the driver's glasses, the weather condition, and the direction of the driver's face. Since, however, the above-mentioned apparatus retrieves and tracks only the eyeballs within the eyeball-existing regions, it erroneously detects the driver's eyebrows or the frame of the glasses when missing the eyeballs due to the presence of the glasses or direct rays reflected from the lenses. In addition, it requires a long processing time because the eye-state detection means 55 tracks the eyeballs by scanning all the vertical pixels in each of the right and left eyeball-existing regions for each horizontal dot for each frame.

SUMMARY OF THE INVENTION

In view of the above, the present invention is intended to solve these problems and has for its object to provide an eye image tracking apparatus that can track images of the eyes of a person accurately without erroneous detection by tracking images of the peripheries of the eyes as well as images of eyes while recognizing missing of the eyes when the eyes have been missed.

An eye image tracking means according to this invention comprises face image input means for inputting an image of the driver's face, digitalizing means for digitalizing the input image of the face, image retrieval means for retrieving images of each of the driver's eyes and its periphery from the digitalized image, and image tracking means for tracking the retrieved images of each eye and its periphery.

In one form of the invention, the image retrieval means comprises means for setting a first eye-extraction region within the digitalized image, first image candidate extraction means for extracting candidates for the images of one eye and its periphery from the eye extraction region, and candidate determination means for determining the images of the one eye and its periphery from the candidate images.

In another form of the invention, the image tracking means comprises means for setting a second eye-extraction region within the digitalized image, second image candidate extraction means for extracting candidates for the images of the other eye and its periphery from the eye extraction region, image correlation means for correlating the extracted candidate images with any images in the previous screen, and image recovery means for recovering, as the image candidates, images that appear again after missing.

In a further form of the invention, the image tracking means further includes eye determination means for accurately tracking images of the eyes based on the results of the correlation executed by the image correlation means.

In a yet further form of the invention, the image correlation means comprises position correlation means for correlating the candidate for the image of the eye extracted by the second image candidate extraction means with an image in the previous screen based on information on the position of the eyes relative to the nostril in the previous screen, duplication elimination means for eliminating the duplication of the correlation, and re-correlation means for correlating any previous image with a candidate that has not been correlated.

In a still further form of the invention, the image correlation means comprises position correlation means for correlating the candidates for the images of the eyes extracted by the image candidate extraction means with any images in the previous screen based on eye position information shown in shape histograms within the eye extraction regions of the previous screen, duplication elimination means for eliminating the duplication of the correlation, and re-correlation means for correlating any previous image with a candidate that has not been correlated.

In a further form of the invention, the eye determination means includes eye candidate pair retrieval means for retrieving images of a pair of the right and left eyes to determine the eyes based on the correlation between the results of the correlation executed by the image correlation means and the eyes retrieved by the eye candidate pair retrieval means.

The above and other objects, features and advantages of the present invention will more readily be understood from the following detailed description of preferred embodiments of the invention when taken in conjunction with the accompanying drawings.

BRIEF DESCRIPTION OF THE DRAWINGS

FIGS. 1(a) and 1(b) show the configuration of an eye image tracking apparatus according to a first embodiment (hereinafter simply referred to as Embodiment 1) of this invention, in which FIG. 1(a) is a block diagram schematically showing an overall configuration of the apparatus, and FIG. 1(b) is a functional block diagram showing various functions thereof;

DETAILED DESCRIPTION OF THE PREFERRED EMBODIMENTS

Figure 1:
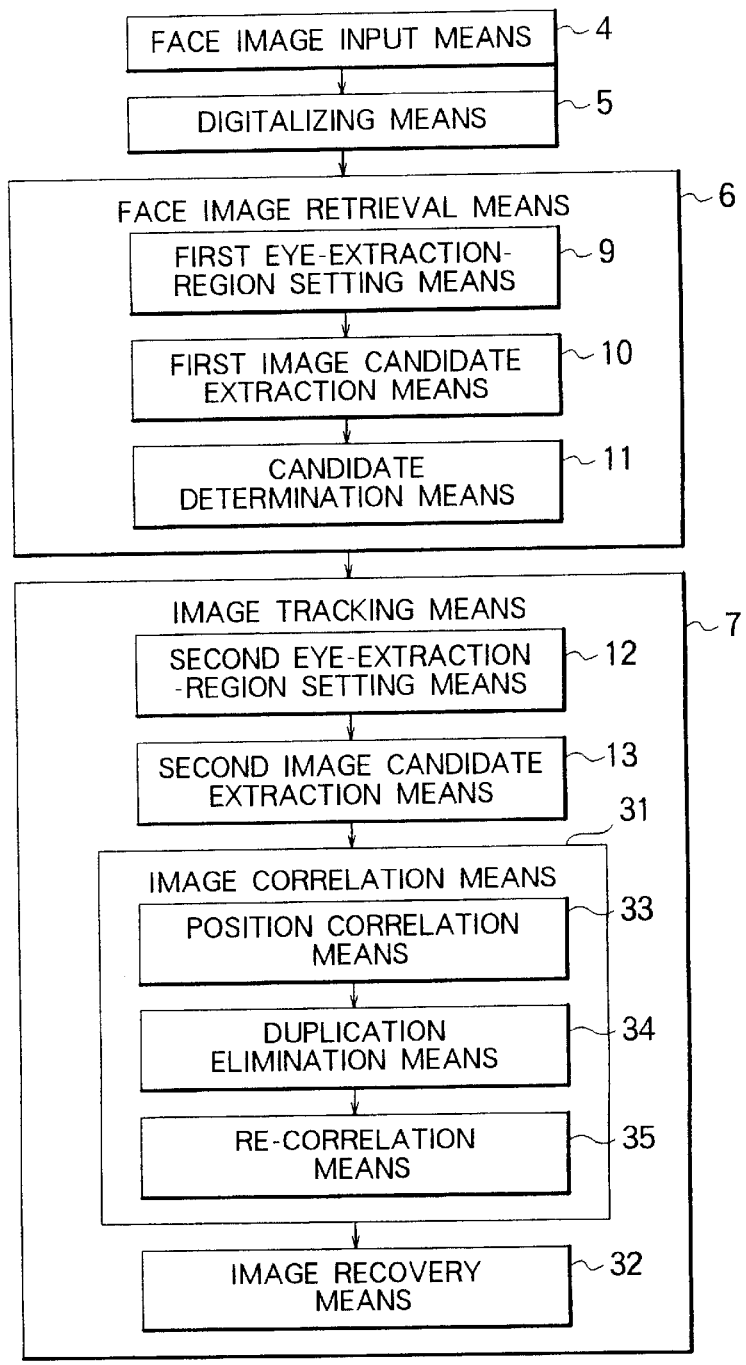

Presently preferred embodiments of the present invention are described below with reference to the accompanying drawings.

Embodiment 1

FIG. 1(a) shows the schematic overall configuration of a face image processor according to Embodiment 1 of this invention. The face image processing device is composed of a photographing device 1 such as a CCD camera that takes a photograph of a driver's face, an image memory 2 for storing the image data in the image of the face output by the photographing device, and a processor 3 such as a CPU that processes images based on data in the image memory 2, as shown in FIG. 1(a).

As shown in FIG. 1(b), the face image processing device comprises a face image input means 4 for inputting the image of the face from the photographing device 1, a digitalizing means 5 for digitalizing the input image of the face, an image retrieval means 6 for retrieving images of each eye and its periphery from the digitalized image, and an image tracking means 7 for tracking the retrieved images of the eye and its periphery.

The image retrieval means 6 comprises a first eye-extraction-region setting means 9 for setting a first eye-extraction region within the digitalized image, a first image candidate extraction means 10 for extracting candidates for the images of one eye and its periphery from the eye extraction region, and a candidate determination means 11 for determining the images of the eye and its periphery from their candidates.

The image tracking means 7 comprises a second eye-extraction-region setting means 12 for setting a second eye-extraction region within the digitalized image, a second image candidate extraction means 13 for extracting candidates for the images of the other eye and its periphery from the eye extraction region, an image correlation means 31 for correlating the extracted candidate images with any images in the previous screen, and an image recovery means 32 for recovering as the image candidates, images that appear again after missing.

The image correlation means 31 comprises a position correlation means 33 for correlating the candidate for the image of the eye extracted by the second image candidate extraction means 13 with an image in the previous screen based on information on the position of the eyes relative to the nostril in the previous screen, a duplication elimination means 34 for eliminating the duplication of the correlation, and a re-correlation means 35 for correlating any previous image with a candidate that has not been correlated.

The position correlation means 33 may correlate the candidate for the image of the eye extracted by the second image candidate extraction means 13 with any image in the previous screen based on eye position information shown in shape histograms of the eye-extraction regions in the previous screen, instead of the information on the position of the eyes relative to the nostril.

The functions of each of the above means are provided by software by the processor 3 executing programs but may be provided by hardware such as electric circuits as required.

Figure 2:
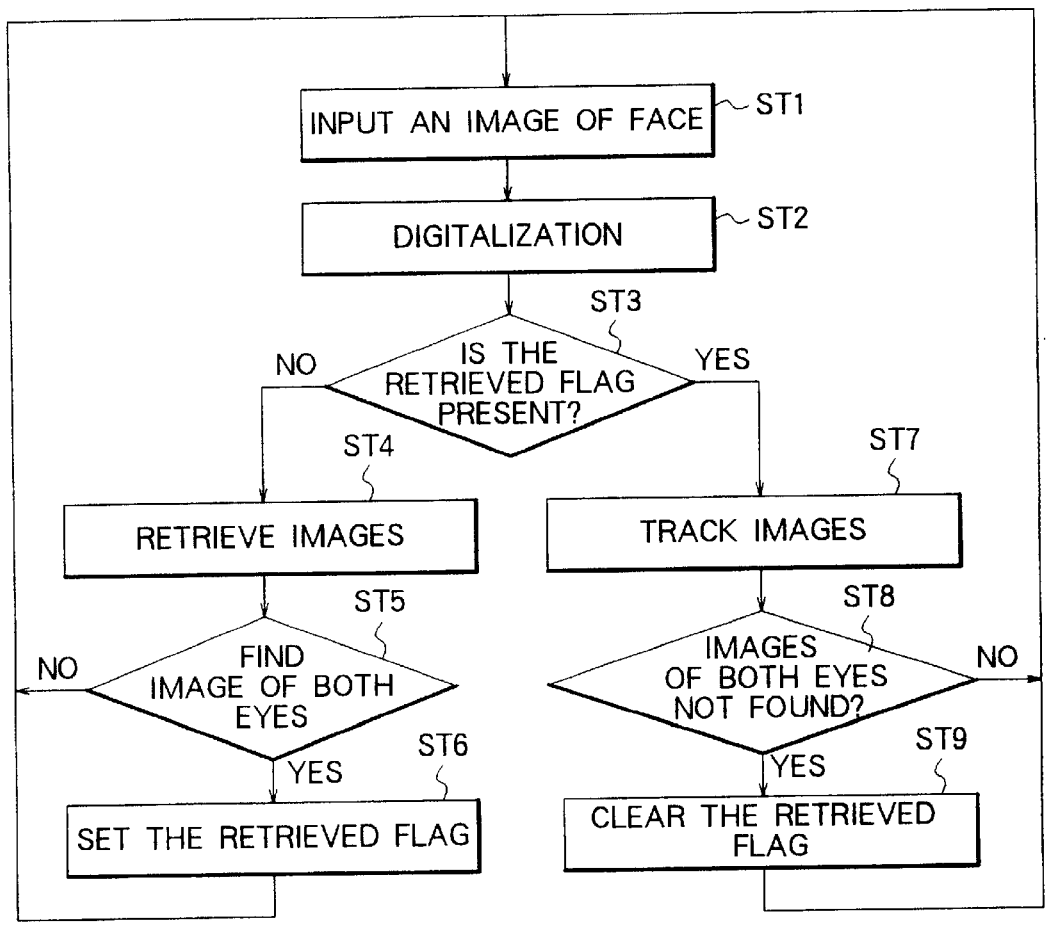
FIG. 2 is a flowchart showing the flow of processing in Embodiment 1.

FIG. 2 is a flowchart showing an outline of the processing in the processor 3 in FIG. 1. In FIG. 2, the face image input means 4 inputs image data on an image of the driver's face to the processor 3 from the image memory 2 (step ST1), and the digitalizing means 5 then digitalizes the data (step ST2). Then, the process determines whether or not a "Retrieved" flag is present (step ST3), and if not, the image retrieval means 6 retrieves images of the eye 7 and its periphery from the digitalized image (step ST4), and determines whether or not the digitalized image contains an image of both eyes (step ST5). If not, the process returns to step ST1, and otherwise sets the Retrieved flag (step ST6) and returns to step ST1.

In addition, if it is determined at step ST3 that the Retrieved flag is present, the image tracking means 7 tracks the retrieved images of the eye and its periphery (step ST7). Then, it is determined whether the digitalized image does not contains an image of both eyes (step ST8). If not (i.e., the image is contained), the process returns to step ST1, and otherwise the Retrieved flag is cleared (step ST9) and then the process returns to step ST1. That is, the process transfers from the image retrieval means 6 to the image tracking means 7 if retrieval has been successful, and otherwise the image retrieval means 6 re-executes retrieval until it succeeds. If it is determined, after the transfer to the image tracking means 7, that both eyes have been missed, the process again returns to the image retrieval means 6 for performing re-retrieval.

The above-mentioned means will be described below in detail.

Figure 3:
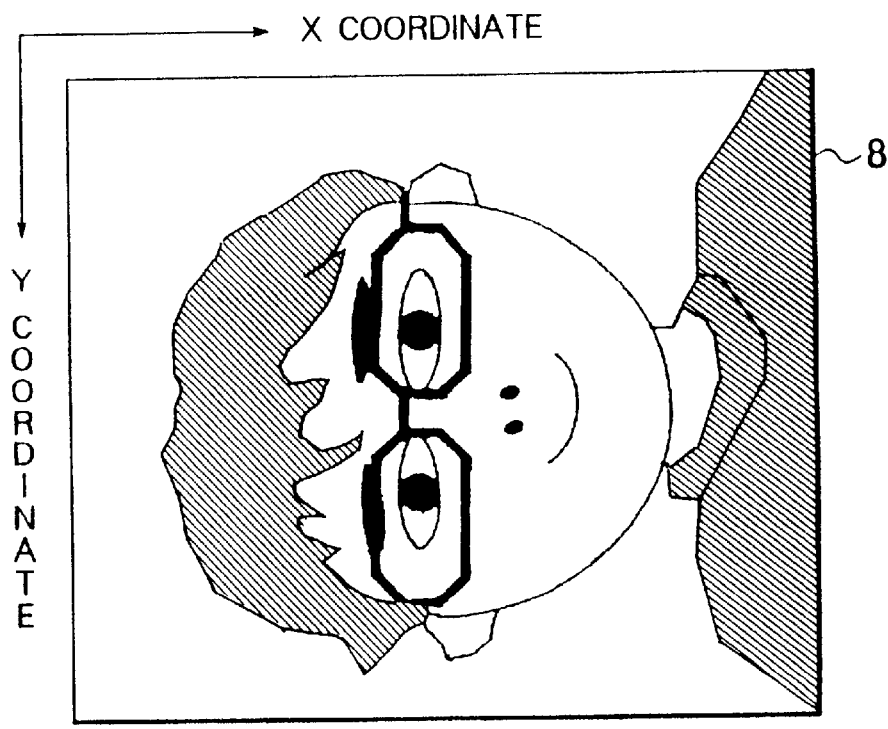
FIG. 3 shows an image input by a photographing device.
Figure 4:
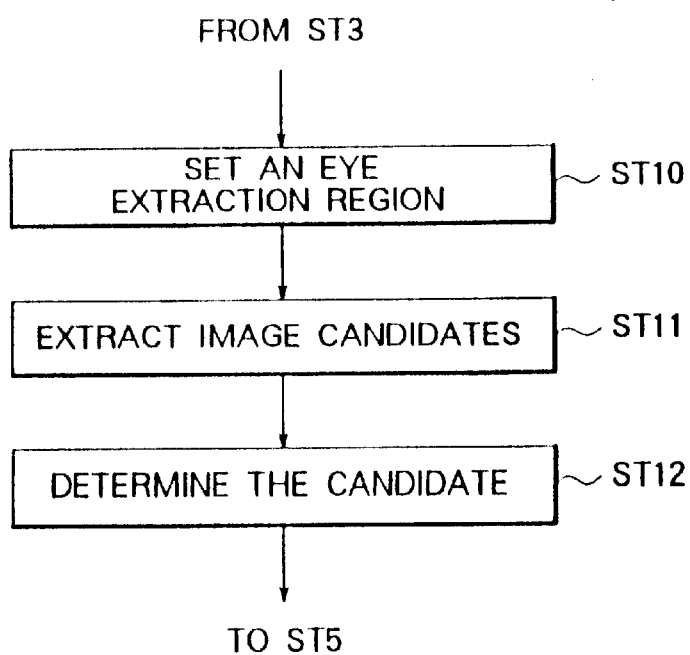
FIG. 4 is an explanatory view of an image retrieval means.
Figure 5:
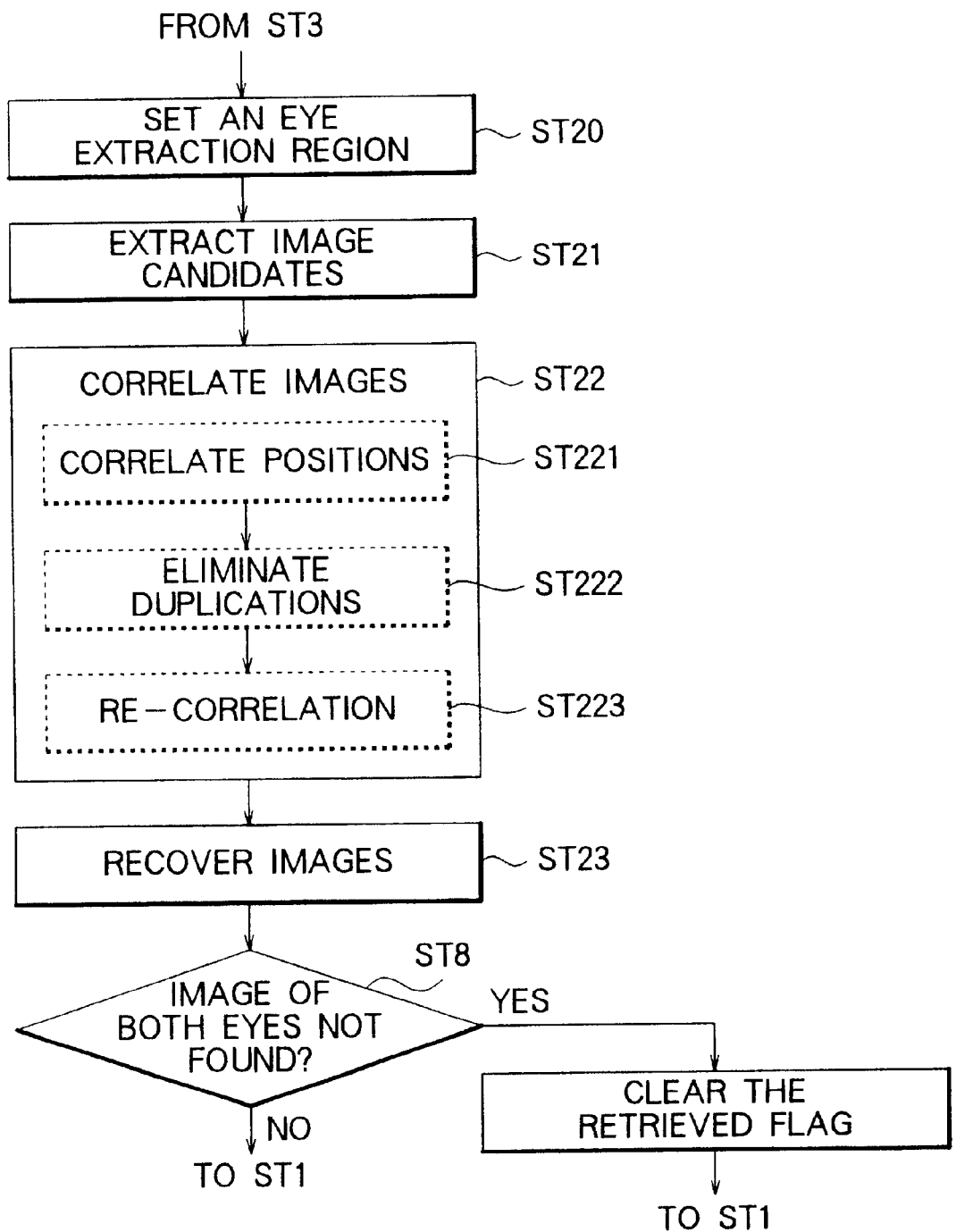
FIG. 5 is a flowchart showing the flow of processing executed by an image tracking means according to Embodiment 1.
Figure 6:
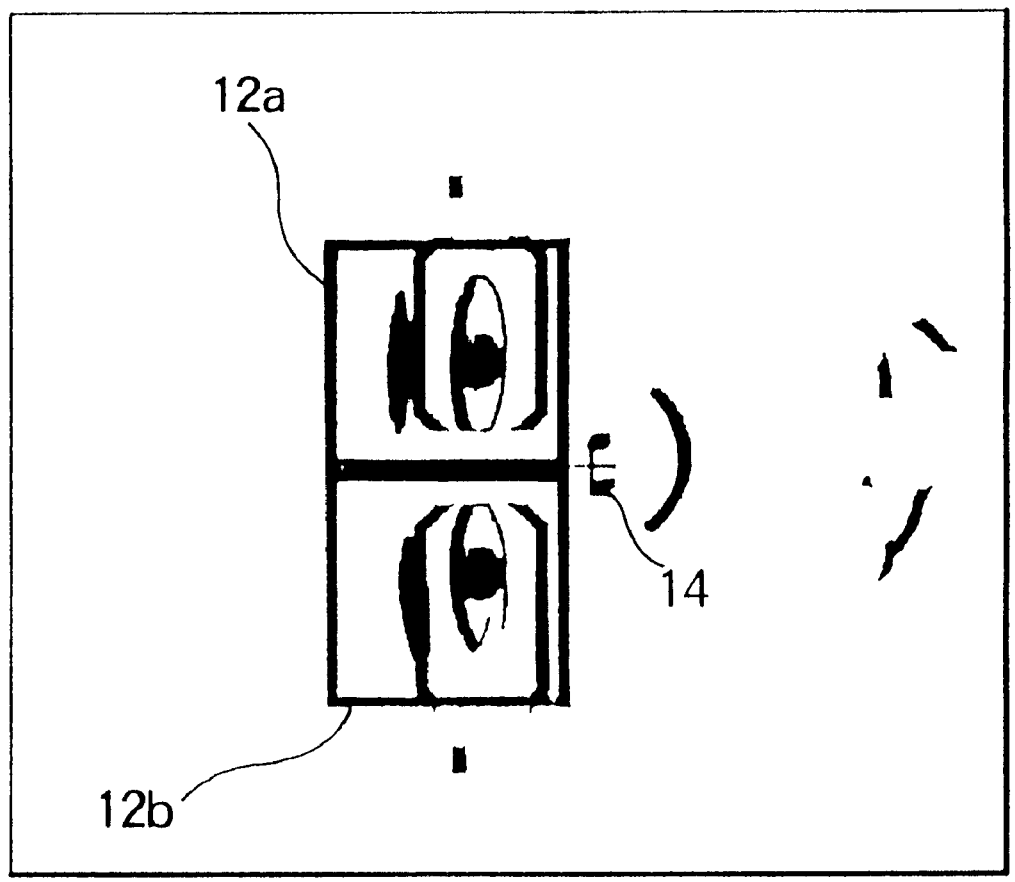
FIG. 6 shows eye extraction regions set by an eye-extraction-region setting means.
Figure 7:
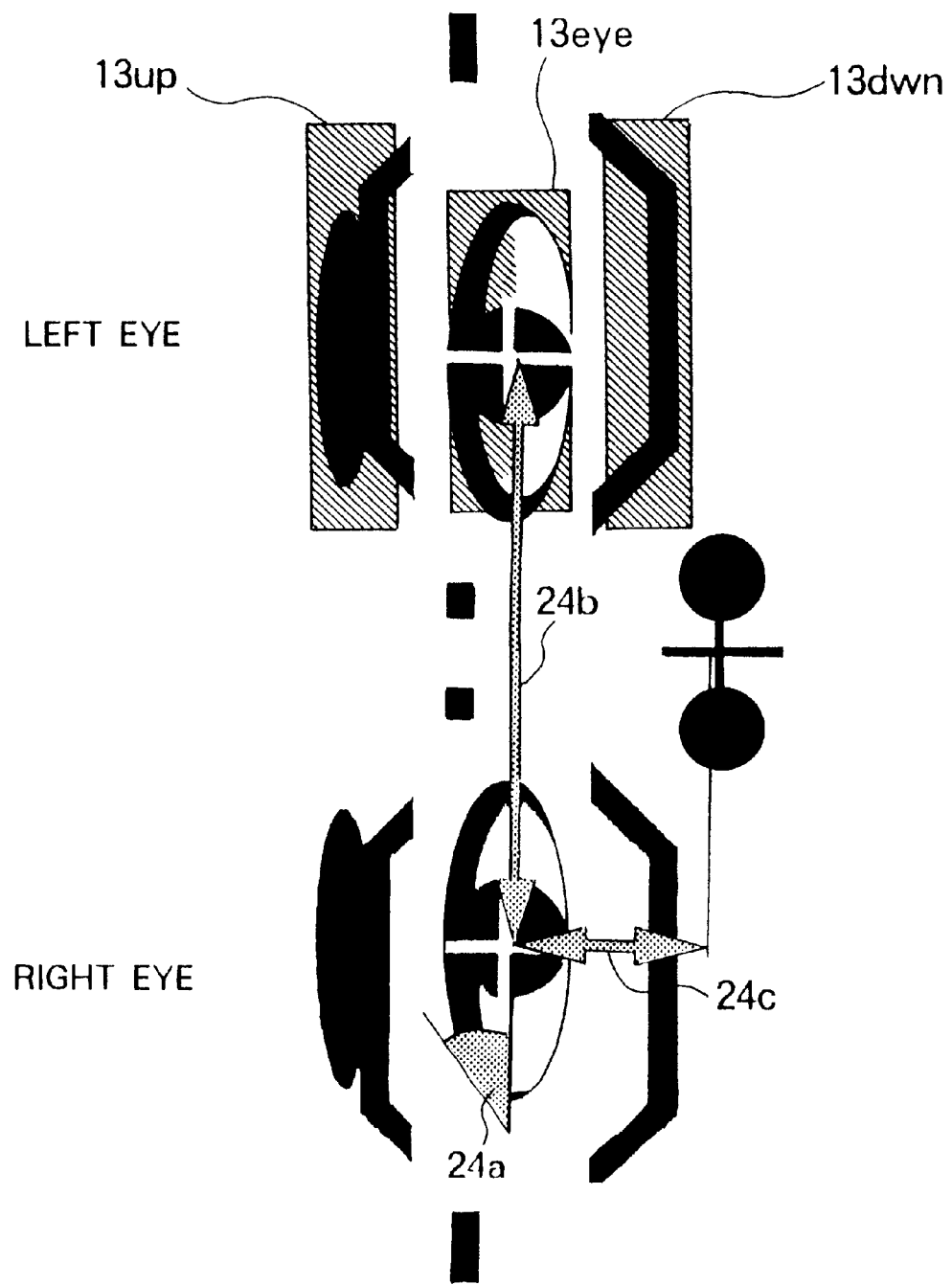
FIG. 7 shows an image of one eye, an image showing a portion above the eye, an image showing a portion below the eye retrieved by the image retrieval means, and part of evaluation function values.

FIG. 3 shows an image of the face 8 photographed by the photographing device 1. FIGS. 4 and 5 are flowcharts showing an outline of processing executed by the image tracking means 7. FIG. 6 shows eye extraction regions 12a, 12b set by the eye-extraction region setting means 9. FIG. 7 shows an image of each eye "13eye" and images of the periphery of the eye "13up" and "13dwn" that have been extracted.

As shown in the flowchart of FIG. 4, the image retrieval means 6 uses the first eye-extraction-region setting means 9 to set eye extraction regions within a digitalized image (step ST10). That is, the first eye-extraction-region setting means 9 forms windows of a predetermined size in the upper part of the face based on a preset reference position 14 (the center of the nostril in this example). These windows are the eye extraction regions 12a and 12b (FIG. 6).

Then, the first image candidate extraction means 10 extracts candidates for the images of each eye and its periphery within the eye extraction region (step ST11), and the candidate determination means 11 determines the images of each eye and its periphery from their candidates (step ST12).

Figure 8A:
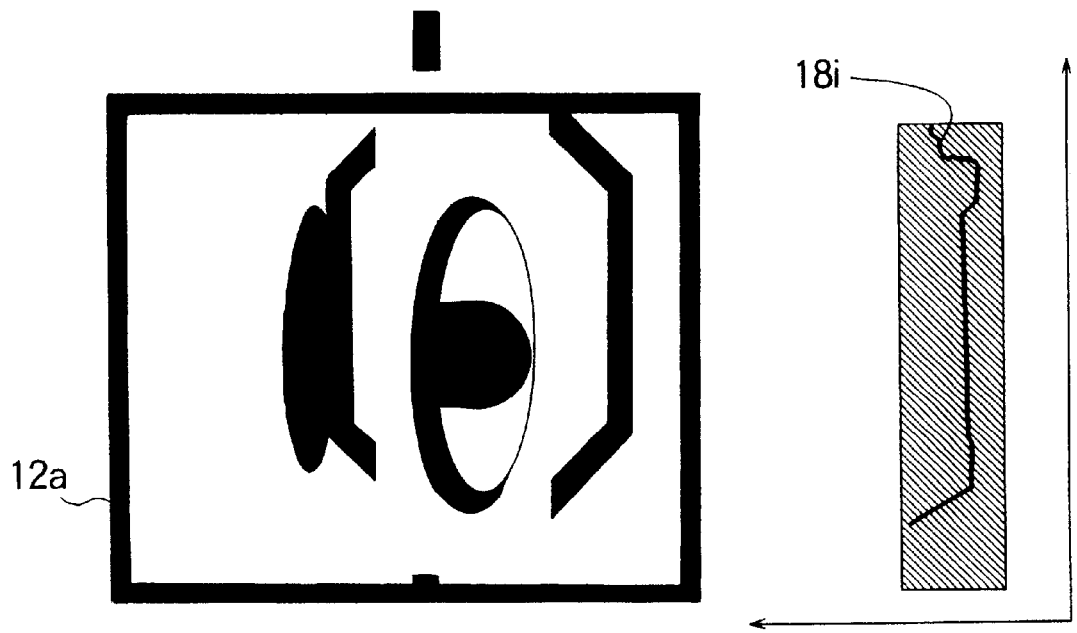
FIG. 8(a) shows an X histogram created within the eye extraction regions.
Figure 8B:
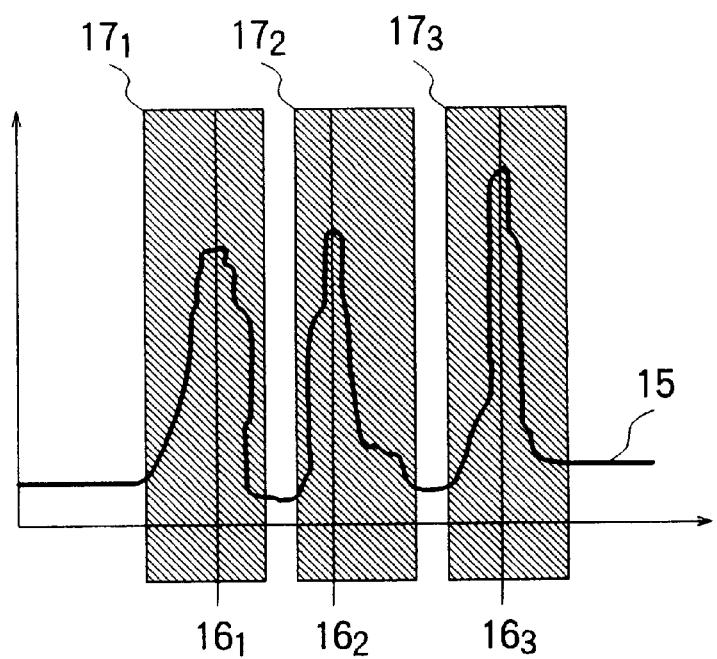
FIG. 8(b) shows a Y histogram created within the eye extraction regions.
Figure 9:
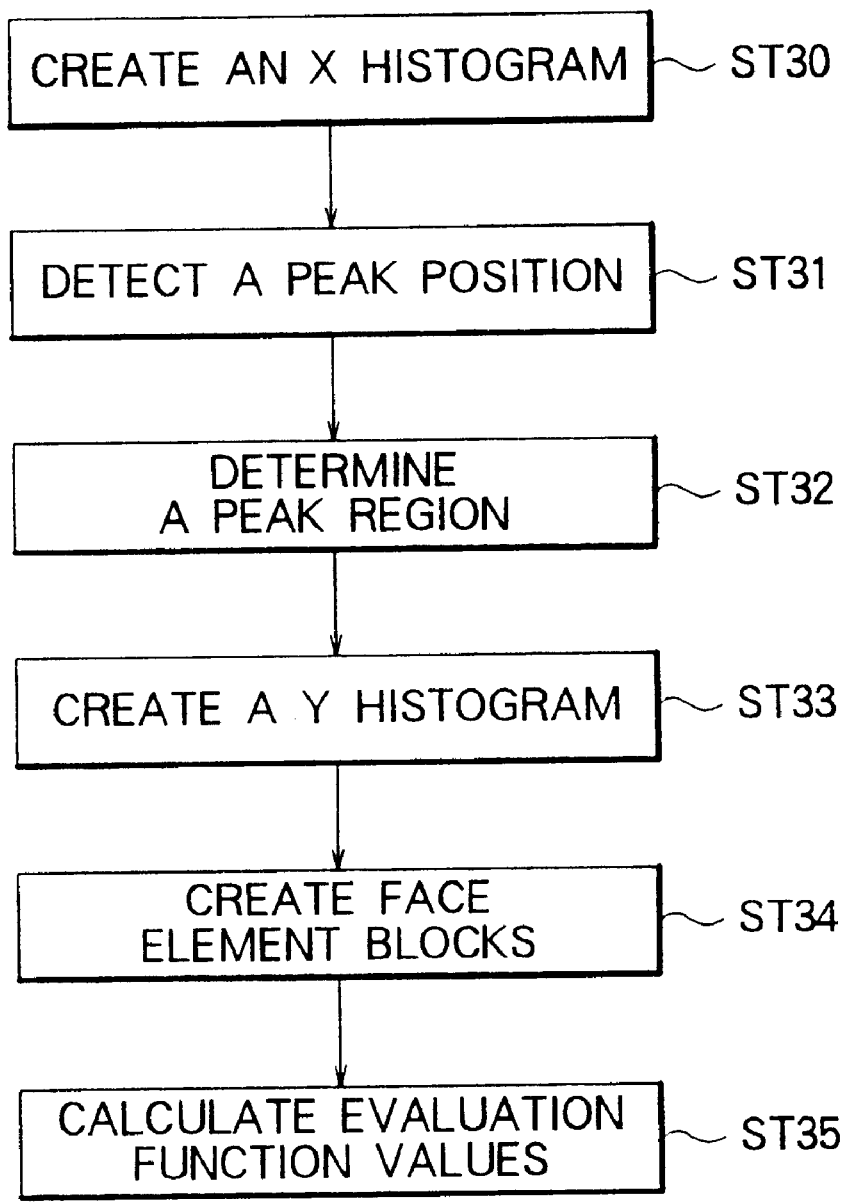
FIG. 9 is a flowchart showing the flow of processing executed by the image retrieval means.
Figure 10:
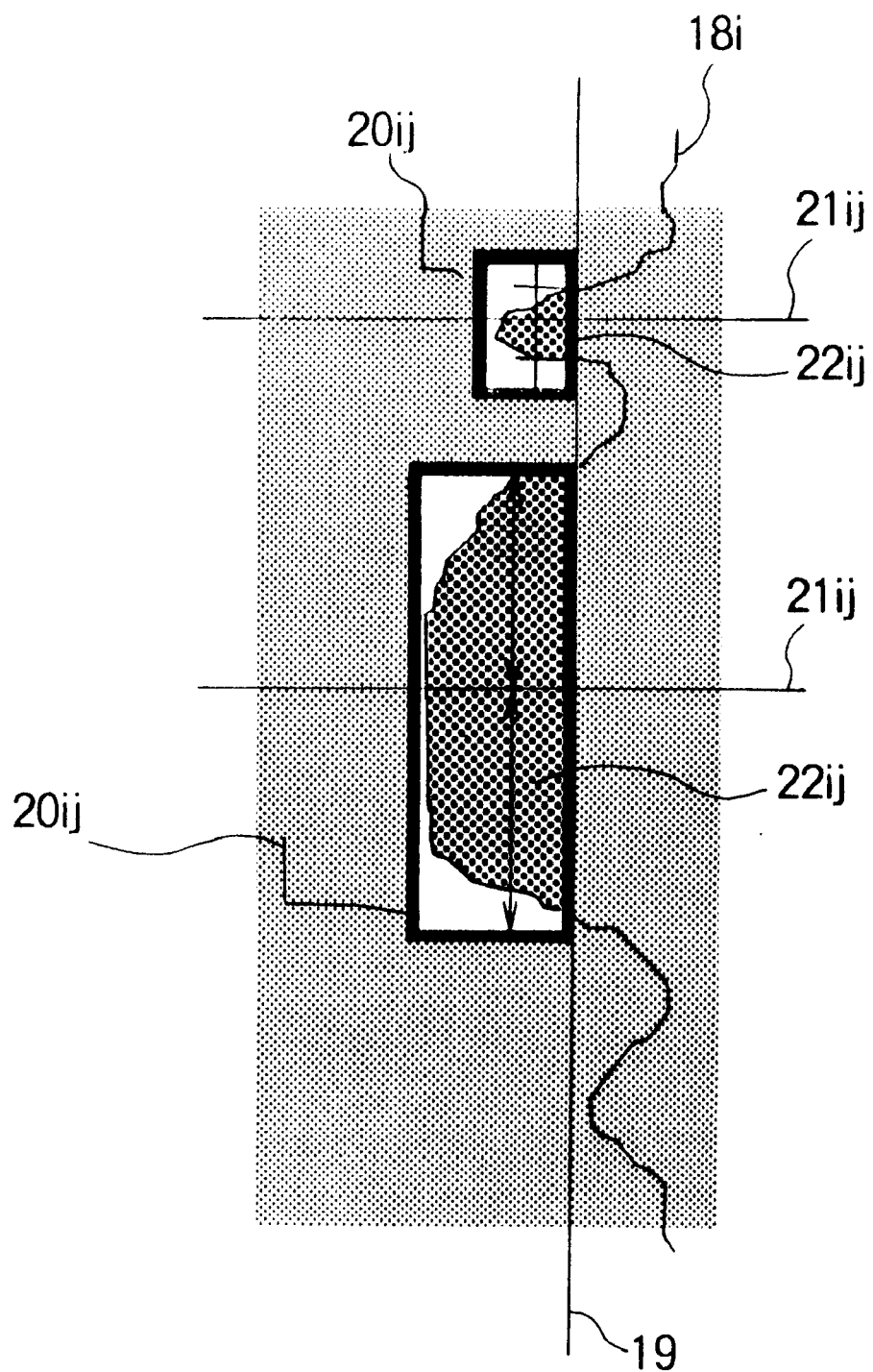
FIG. 10 shows an image blocked by a face element blocking means.

The extraction of candidates for the images of the eye and its periphery executed by the first image candidate extraction means 10 is described below in detail with reference to FIGS. 8(a) to 10. FIGS. 8(a) and 8(b) show an X histogram and a Y histogram, respectively, created within the eye extraction regions. FIG. 9 is a flowchart showing an outline of the processing executed by the first image candidate extraction means 10. FIG. 10 shows part of a procedure for cutting face element block candidates out from the eye extraction regions.

First, as shown in FIGS. 8(a) and 8(b), an X histogram 15 is created that projects the number of the pixels in the direction of the Y axis at each X coordinate in the window (step ST30), and then a peak position 16i and a peak region 17i are detected in which a face element may be present (steps ST31 and ST32). Furthermore, a Y histogram 18i is created that projects the number of the pixels in the direction of the X axis at each Y coordinate in each peak region (step ST33). In the Y histogram 18i, a threshold 19 is set; a face element block candidate 20ij is cut out; and the middle point 21ij of the face element block candidate in the direction of the Y axis and the area 22ij of the block candidate are calculated (step ST34).

This processing is executed in each of the right and left eye extraction regions. Finally, the candidate determination means 11 calculates an evaluation function value and creates a pair of right and left candidates to determine whether or not they are candidates for the images of the eyes and their periphery (step ST35). The right and left candidates pair indicates those candidates which are likely to be images of eyes or their periphery among combinations of a face element block candidate within the left-eye extraction region and a face element block candidate within the right-eye extraction region. In this embodiment of the invention, the evaluation function value may be the inclination of the corners of the eyes in the candidates 24a, the relative positions of the right and left candidates 24b, and the positions of the right and left candidates relative to the nostril 24c, as shown in FIG. 7.

If any pair meets the evaluation function values 24a to 24c, it is determined to be the images of the eyes "13eye". If any face element blocks are present above and below the images of the right and left eyes, they are determined to be the images of the periphery of the eyes "13up" and "13dwn". The number of the peak region NO.i in which the images of the eyes and their periphery are present, all the peak positions 16i, all the middle points in the direction of the Y axis 21ij, the area of the region 22ij, and the evaluation function values 24a to 24c for the images of the eyes are stored in the memory. If any such pair or block are not present, the process returns to the first eye-extraction-region setting means 9 to repeat the above processing.

The processing executed after the retrieval of the images of the eyes and their periphery is described below.

After the images of the eyes and their periphery have been successfully detected, the process proceeds to the processing executed by the image tracking means 7 (step ST7), as shown in the flowchart of FIG. 2. The details of the processing by the image tracking means 7 are as shown in the flowchart of FIG. 5.

First, the second eye-extraction-region setting means 12 for setting eye extraction regions within the digitalized image forms windows of a predetermined size in the upper part of the face based on the reference position 14 (FIG. 6) (step ST20). The second image candidate extraction means 13 then extracts candidates for the images of each eye and its periphery (step ST21). These operations are the same as in the image retrieval means 6.

Next, the image correlation means 31 correlates the images in the previous screen with the images in the current screen (step ST22), and the image recovery means 32 recovers missing images (step ST23).

Then, it is determined whether or not the correlation has been successful (whether or not images of both eyes are present) (step ST8). If yes, the process continues tracking and otherwise returns to the retrieval. The image correlation means 31 comprises a position correlation means 33, a duplication elimination means 34, and a re-correlation means 35. The processing in the image correlation means 31 is described below with reference to FIG. 5.

The position correlation means 33 first executes a correlation using the peak position 16ib and the peak region 17ib of the previous screen set by the second image candidate extraction means 13 (or the first image candidate extraction means 10) and the peak position 16i and the peak region 17i in the current screen (step ST221).

The position correlation is carried out as follows. Between the peak numbers No. i in the current screen (starting number: "0"; last number: "end") and all the peak numbers "NO.ib" (starting number: "0"; last number: "endb") in the previous screen, errors "dx" and "dy" in the distance between the nostril and the eyes in the X and Y directions, respectively, are calculated to obtain "Dxy". For example, "Dxy" applies a weight in the X direction to account for the variation in the Y direction caused by changes in the digitalized form of the eyes as in the following Equation 36.

$$Dxy = 3*dx + dy \quad \text{Equation 36}$$

The peak number "NO.ibk" in the previous screen that has the smallest "Dxy" (="Dmin") relative to the peak number "NO.i" in the current screen is determined to be a corresponding peak, and an array Pn[i]=ibk and the corresponding "Dmin" array "Dm[i]=Dmin" are created. The processing by the position correlation means 33 is thus finished (step ST 221). The smallest "Dxy", however, is inappropriate if its position is significantly different from the corresponding "Dxy" in the previous screen. Thus, a threshold "SDxy" for "Dxy" is set, and for those peaks that can be correlated with no peaks in the current screen, for example, data such as "Pn[i]=NO_VALUE (=0xff)" is saved indicating that the peaks have no correlation.

Of course, since the number of peaks and their positions in the previous screen are not always equal to those in the current screen, there may be a duplicate peak number "NO.ib" (for example, when the number of peaks in the current screen is 4 and the number of peaks in the previous screen is 3, two peak numbers, that is, peak numbers "No. i=2 and 3" may correspond to peak number "NO.ib =2") and those peak numbers "No.i" in the previous screen that cannot be correlated with no peak numbers in the current screen. Such a case is dealt with by the duplication elimination means 34 and the re-correlation means 35.

Figure 11:
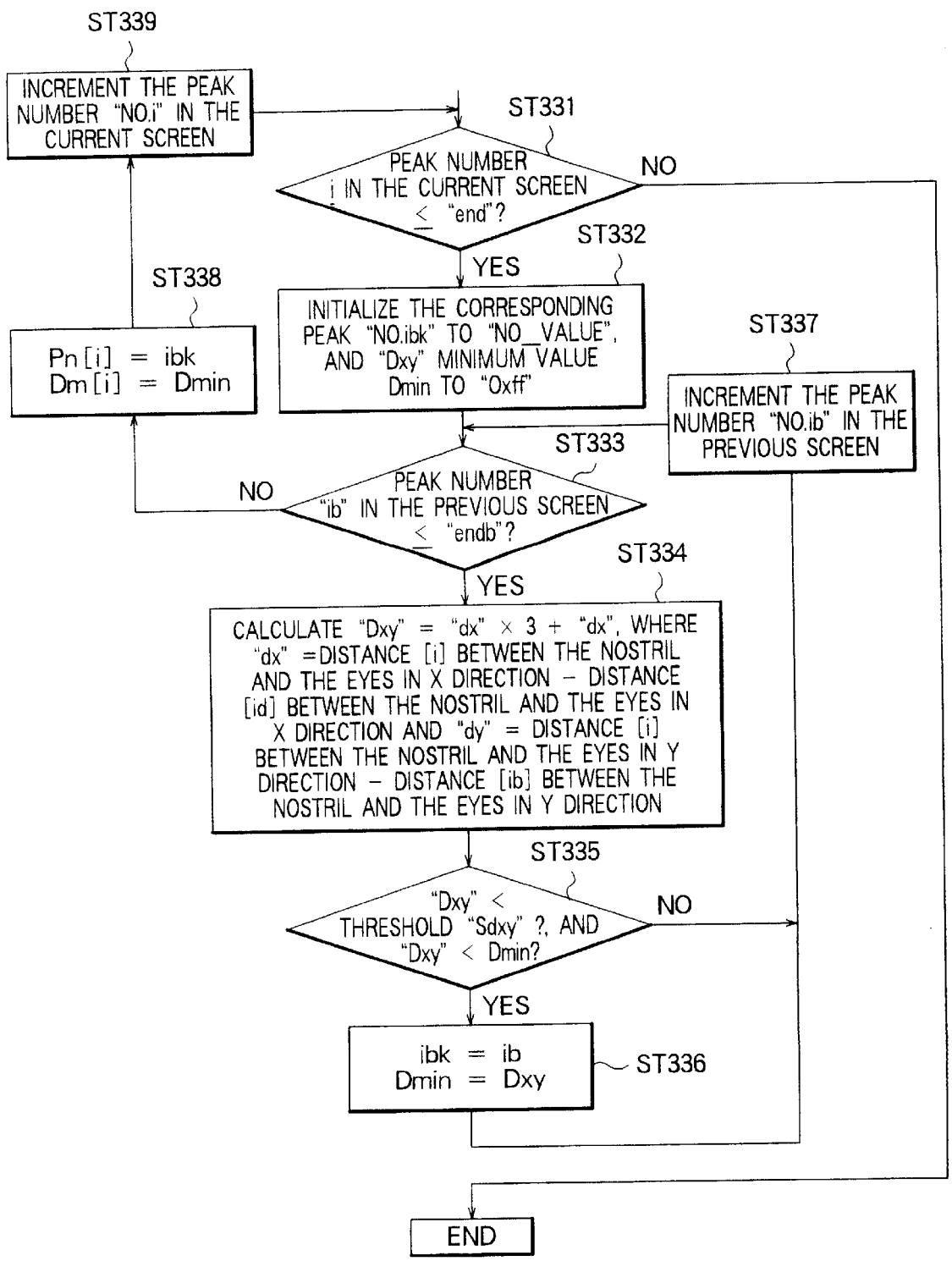
FIG. 11 is a flowchart showing the flow of processing executed by a position correlation means according to Embodiment 1.

Next, the operation of the position correlation means 33 is described in detail with reference to FIG. 11. First, at step ST331, it is determined whether or not the peak numbers "NO. i" in the current screen are larger than the last number "end" (i.e., the loop is repeated for all the peaks in the current screen). If yes (i.e., the answer is positive), the processing is finished and otherwise the corresponding peak number "NO.ibk" is initialized with "NO_VALUE" (i.e., a value indicating no correlation), and the minimum value "Dmin" of "Dxy" is initialized with a value "0xff"and the peak number "NO.ib" in the previous screen is initialized with zero.

Then, during the following step ST333 and subsequent steps, deviations in distance between the nostril and the eyes in directions X and Y are determined between the peak numbers "NO.i" in the current screen and the peaks in the previous screen, and based on the results of which re-correlation is carried out. First, at step ST333, it is determined whether or not the peak numbers "NO.ib" in the previous screen are larger than the last number "endb" (i.e., the loop is repeated for all the peaks in the previous screen). If not, "Dxy" is calculated based on the deviations "dx" and "dy" in the distance between the nostril and the eyes in directions X and Y, respectively, between the peak numbers "NO.i" in the current screen and the peak numbers "NO.ib" in the previous screen (step ST334). If "Dxy" is smaller than the predetermined threshold "SDxy" and also smaller than "Dmin" (step ST335), the corresponding peak number "NO.ibk" and the minimum deviation value "Dmin" are updated (step ST336), and the peak number "NO.ib" in the previous screen is incremented (step ST337), and then the process returns to step ST333 (i.e., the corresponding peak is determined which has a deviation that is smaller than the predetermined threshold "SDxy" and that also has the minimum value). If the condition at step ST335 is not met, the process proceeds to step ST337 while skipping step ST336. If the peak number "NO.ib" is larger than "endb" at step ST333, the corresponding peak number "NO.ibk" is held in the array Pn[i], and the minimum value "Dmin" is held in the array Dm[i] at step ST338 (i.e., the corresponding peak is determined), and then the peak number "NO.i" in the current screen is incremented at step ST339, and thereafter the process returns to step ST331.

Figure 12A:
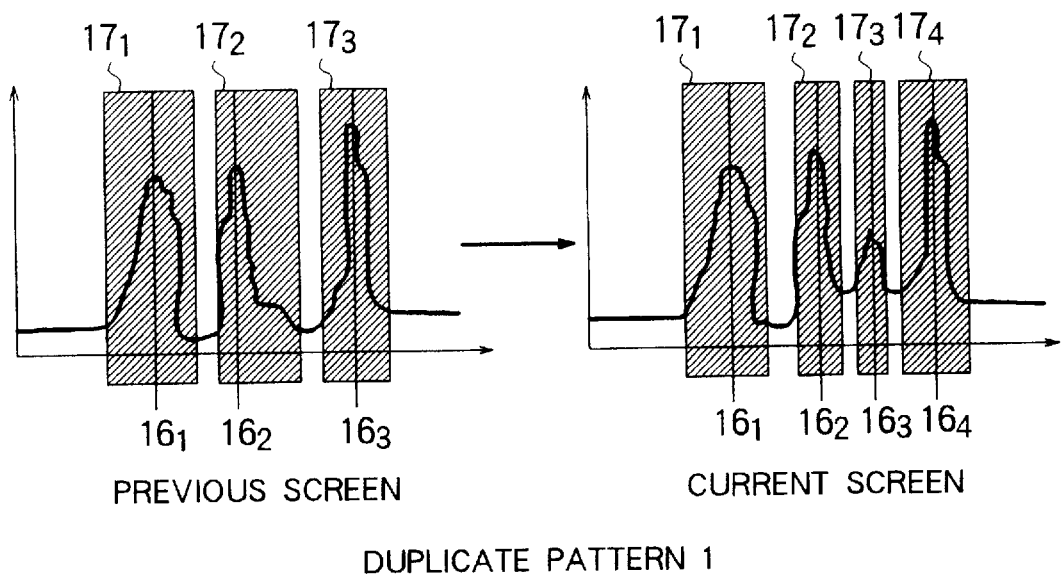
FIGS. 12(a) and 12(b) show different examples of duplication resulting from correlation.
Figure 12B:
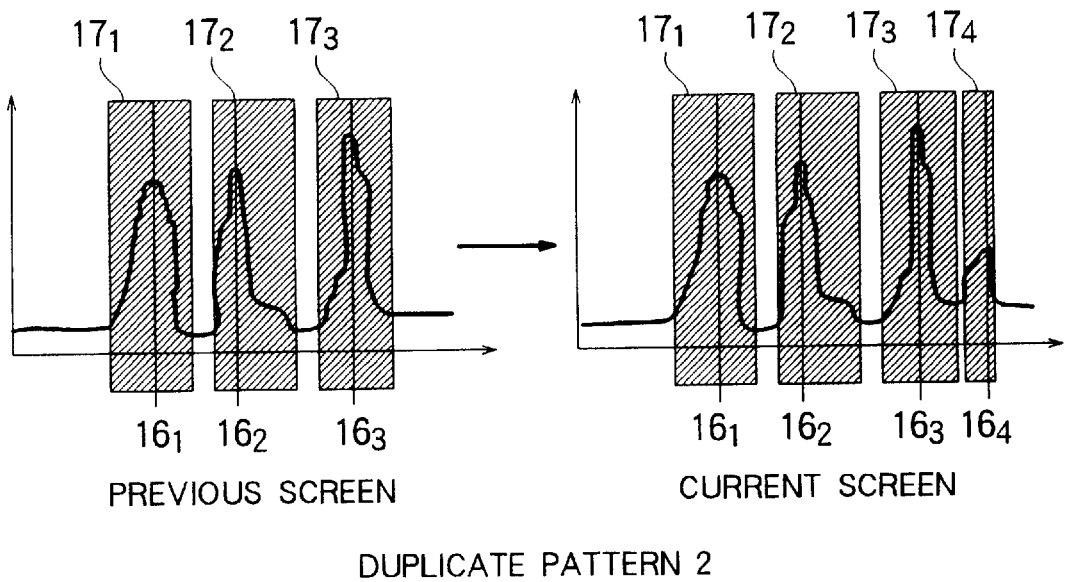

Step ST222 in FIG. 5 shows the processing executed by the duplication elimination means 34 when there is a duplicate peak number "NO.ib" in the previous screen as described above. It is assumed that the number of peaks in the current screen is 4 while the number of peaks in the previous screen is 3 and that two peak numbers "NO.i=2 and 3" correspond to peak number "NO.ib=2", as described above. In such a case, two patterns are possible for example, as shown in FIGS. 12(a) and 12(b). First, a new peak may appear between peak numbers "NO.ib=2 and 3" in the previous screen, as shown in FIG. 12(a). Second, a new peak may follow peak number "NO. ib=3" in the previous screen as in FIG. 12(b). Although the case is taken here in which two peak numbers in the current screen corresponding to one peak number in the previous screen exist, the duplication elimination means 34 performs the following processing while taking account of a case in which there are three peak numbers in the current screen corresponding to one peak number in the previous screen.

Figure 13:
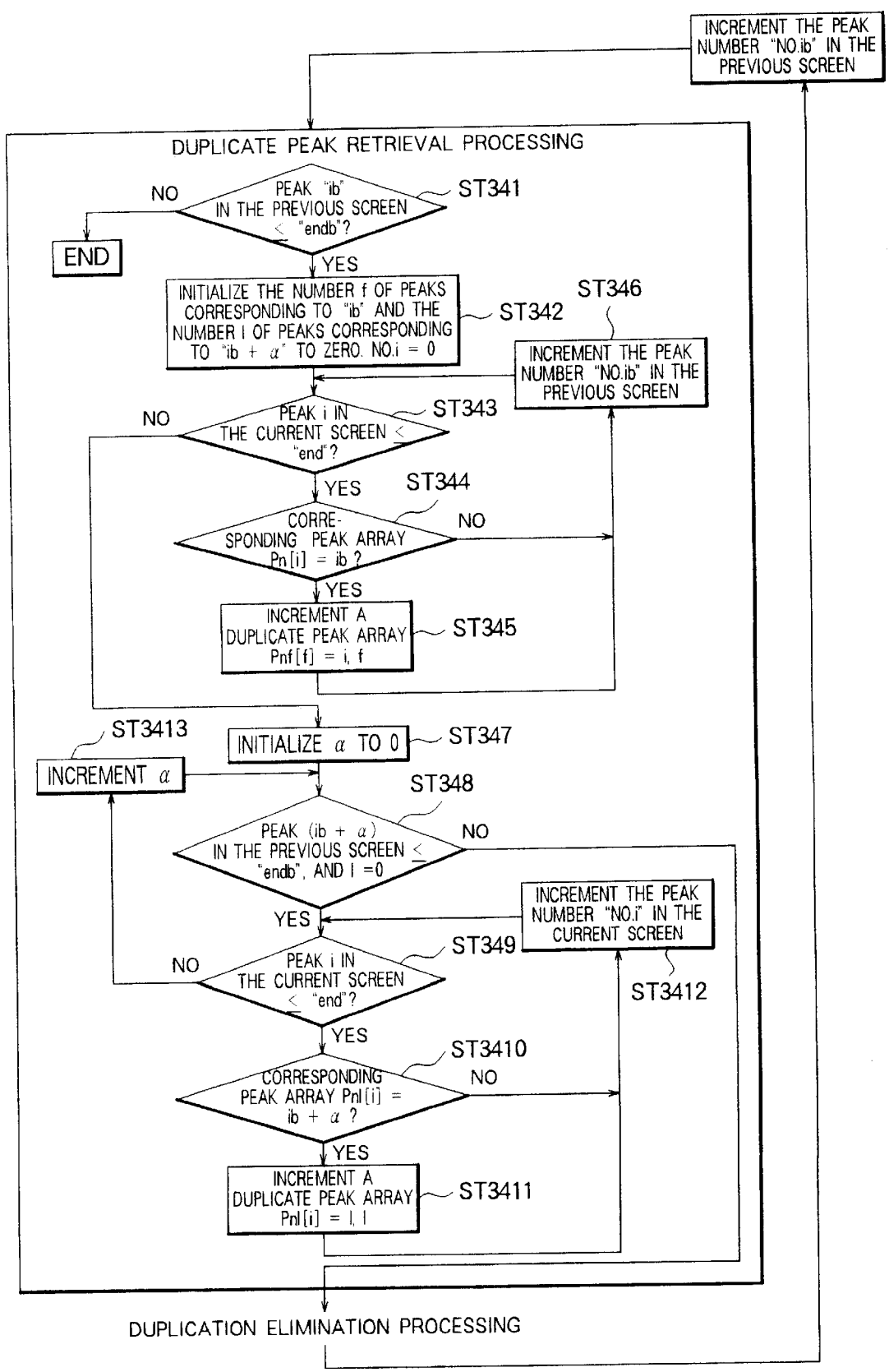
FIG. 13 is a flowchart showing the flow of processing executed by a duplicate peak retrieval section in a duplication elimination means.
Figure 14:
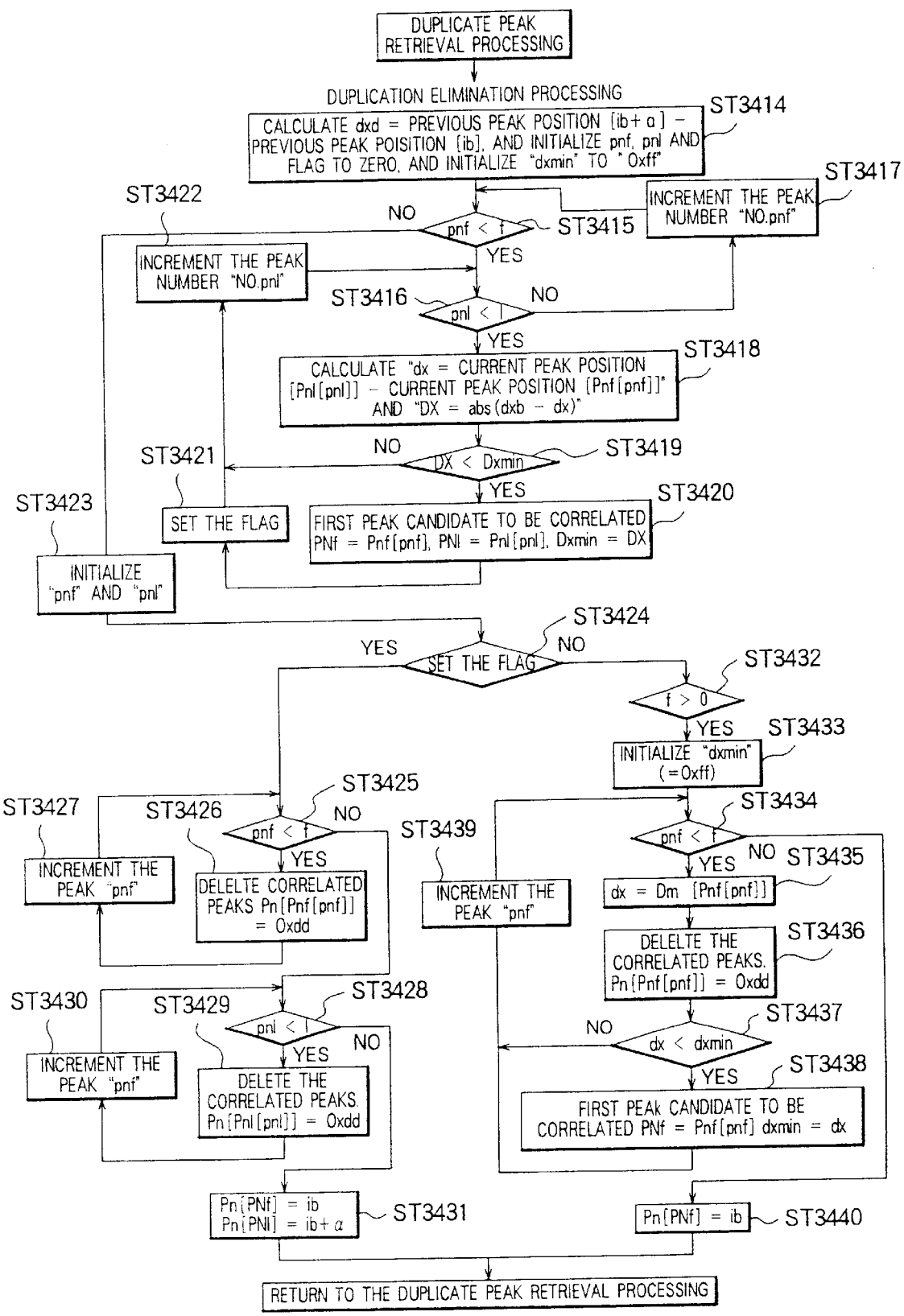
FIG. 14 is a flowchart showing the flow of processing executed by a duplication elimination section in a duplication elimination means.

Here, it is to be noted that the duplication elimination means 34 comprises a duplication retrieval section and a duplication elimination section, and the processing executed by each section is schematically shown in the flowcharts of FIGS. 13 and 14.

First, in FIG. 13, the duplication peak retrieval section retrieves the peak number "NO.i" in the current screen corresponding to the peak number "NO.ibd" in each previous screen to create a duplication peak array "Pnf[f]=i" (herein f designates the number of peaks corresponding to the peak number "NO.ibd"). It subsequently retrieves the peak numbers "NO.i" in the current screen corresponding to the peak number "NO.ib+α" in the previous screen to create a peak array "Pnl[l]=i" (here l designates the number of peaks corresponding to the peak number "NO.ib+α"). α is sequentially incremented for retrieval until "Pnl" is present or until the peak number "NO.ib+α"="endb".

Next, the duplication retrieval processing is specifically described with reference to FIG. 13. At step ST341, it is determined whether or not the peak numbers "NO. ib" in the previous screen are smaller than "endb" (i.e., the loop is repeated for the number of peaks in the previous screen). If not, the process is finished. If yes, the number f of those peaks in the array "Pn[i]" set during the position correlation in step ST342 that correspond to "ib" is initialized to zero, and the number l of peaks corresponding to "ib+α" is also initialized to zero. Also, the peak number "NO.i" in the current screen is initialized to zero.

Then, during step ST343 and subsequent steps, the process retrieves peaks corresponding to the peak "ib" in the previous screen from the array Pn[i]. First, at step ST343, it is determined whether or not the peak number "NO.i" in the current screen is smaller than the value "end" (i.e., the loop is repeated for the number of peaks in the current screen). If not, the process proceeds to step ST347, and otherwise it goes to step ST344 in which it is determined whether or not the corresponding peak array Pn[i] matches the peak numbers "NO.ib" in the previous screen. If yes, the peak i in the current screen is set in the duplication peak array "Pnf[f]" at step ST345, and f and the peak number "NO.i" in the current screen are incremented (step ST346), and thereafter the process returns to step ST343. Otherwise, the process transfers to step ST346 while skipping step ST345.

If the peak number "NO.i" in the current screen becomes larger than the value "end", the process goes to step ST347 where α and the peak number in the current screen is initialized. During the following step ST348 and subsequent steps, the peak corresponding to the peak "ib+α" in the previous screen is retrieved. First, it is determined at step ST348 whether or not the peak number "NO.ib+α" in the previous screen is smaller than the value "endb" and whether or not l is 0 (the loop is repeated for the number of peaks in the previous screen or as long as there are no peaks corresponding to the peak number "NO.ib+α" in the previous screen).

If the peak number "NO.ib+α" in the previous screen is larger than the value "endb" or if l is larger than 0, the process proceeds to the duplication elimination processing, and otherwise it goes to step ST349 where it is determined whether or not the peak number "NO.i" in the current screen is smaller than the value "end" (the loop is repeated for the number of peaks in the current screen). If not, α is incremented (step ST3413) and the process returns to step ST348. Otherwise, it is determined at step ST3410 whether or not the corresponding peak array "Pn[i]" matches the peak number "NO.ib+α" in the previous screen. If yes, the peak i in the current screen is set in the duplication peak array "Pnl[l]" at step ST3411, and l is incremented and the peak number "NO.i" in the current screen (step ST3412), and returns to step ST349. Otherwise, the process transfers to step ST3412 while skipping step ST3411.

In FIG. 14, if both the number f of peaks corresponding to the peak number "NO.ib" and the number l of peaks corresponding to the peak number "NO.ib+α" are positive, one of the created combinations of the peak arrays "Pnf" and "Pnl" that is closest to the position relationship between the peak numbers "NO.ib" and "NO.ib+α" is determined to be the correct correlation to thereby modify the corresponding peak array Pn. In addition, if only the number of peaks f corresponding to the peak number "NO.ib" is positive, the peak with the smallest "D min" array "Dm[i]=Dmin" obtained when the position correlation means 31 has provided a correlated peak array "Pn[i]=ibk" is determined to be the correct correlation to thereby modify the corresponding peak array "Pn". Any data indicating the deletion of a peak from the peak array "Pnf" or "Pnl" is saved (for example, data such as the corresponding peak array "[i]=DELETED" (="Oxdd") is correlated with such peaks, indicating that those peak numbers NO. are not present).

Next, the duplication elimination processing is described with reference to FIG. 14. At step ST3414, the deviation "dx" between the position of the previous peak "ib+α" and the current peak "ib" is calculated, and the number of determined peak numbers "NO.pnf" and "NO.pnl" and the Candidate Presence flag are initialized to zero and the minimum value "dxmin" of "dxb" is initialized to "Oxff". Then, during the following step ST3415 and subsequent steps, one of the combinations of peaks correlated with the previous peaks "ib+α" and "ib" is selected that is likely to be the most correct, in order to eliminate duplication. At step ST3415, it is determined whether or not "pnf" is smaller than f (i.e., the loop is repeated for the number of peaks with "ib" correlated with the counterpart in the current screen). If yes, it is then determined at step ST3416 whether or not "pnl" is smaller than l(the loop is repeated for the number of peaks with "ib+α" correlated with the counterpart in the current screen). If yes, "pnf" is incremented at step ST3417, and "pnl" is initialized to zero, and the process returns to step ST3415. Otherwise, the deviation between the position of the current peak "Pnl[pnl]" and the position of the current peak "Pnf[pnf]" is calculated, on the basis of which the deviation "DX=abs (dxb−dx)" is calculated.

Subsequently at step ST3419, it is determined whether or not "DX" is smaller than the minimum value "Dxmin". If not, "Pnl" is incremented at step ST3422 and the process returns to step ST3416. Otherwise, at step ST3420, the correlated first peak candidates "PNf", "PNl", and "Dxmin" are updated to "Pnf", "Pnl", and "DX", respectively (that is, a combination for the minimum deviation "DX" is selected). If there is any first peak candidate (i.e., the process passes step ST3420), the Candidate Presence flag is set (step ST3421) and the process goes to step ST3422.

If "pnf" becomes larger than f at step ST3415, the process proceeds to step ST3423 in which "pnf" and "pnl" are initialized, and then at step ST3424, it is determined whether or not the flag is set.

If the flag is set, the processing from step ST3425 to ST3431 is carried out. That is, the peaks having been correlated with "ib" and "ib+α" by the position correlation means 31 are deleted and only the first candidate obtained at step ST3420 is set again. Otherwise, the processing from step ST3432 to ST3440 is performed, that is, the peaks having been correlated with "ib" by the position correlation means 31 are deleted and only the peak with the smallest deviation between the nostril and the eyes is set again.

First, it is determined at step ST3425 whether or not "pnf" is smaller than f, and if yes, the correlated peak is deleted and Oxdd is set in "Pn[Pnf[pnf]]" to indicate that those peaks have been deleted at step ST3426. Subsequently, "pnf" is incremented at step ST3427 and the process returns to step ST3425. If "pnf" is larger than f, the process proceeds to step ST3428 in which it is determined whether or not "pnl" is smaller than l, and if yes, the correlated peaks are deleted and Oxdd is set in "Pn[Pnl[pnl]]" to indicate that those peaks have been deleted at step ST3429. Subsequently, "pnl" is incremented at step ST3430 and the process returns to step ST3428. If "pnl" is larger than l, "Pn[PNf]" and "Pn[PNl]" are set to "ib" and "ib+α", respectively, at step ST3431, and the process is thus finished.

Next, it is determined at step ST3432 whether or not f is present (f>0). If yes (f>0), the minimum value "dxmin" of the distance between the nostril and the eyes is initialized to "Oxff" at step ST3433. Subsequently at step ST3434, it is determined whether or not "pnf" is smaller than f. If yes, "dx=Dmin[Pnf[pnf]]" (I.e., the array held for position correlation) is invoked at step ST3435, and the correlated peaks are deleted with Oxdd being set in "PN[Pnf[pnf]]" to indicate that those peaks have been deleted, at step ST3436. It is determined at step ST3437 whether or not "dx" is smaller than "dxmin", and if yes, the correlated first peak candidate "PNf" and the minimum value "dxmin" are updated at step ST3438 and "pnf" is incremented at step ST3439. Otherwise, the process proceeds to step ST3439 without carrying out step ST3438. If "pnf" becomes larger than f, "ib" is set in "Pn[PNf]" at step ST3440, thus finishing the processing.

The processings by the duplicate peak retrieval section and the duplication elimination section are repeated until the peak number "NO.ib=endb".

The re-correlation means 35 executes processing if there is any peak number "NO.i" in the current screen which has not been correlated. Let us consider that any peak has not been correlated by the position correlation means 35 or is erroneously correlated and then deleted by the duplication elimination means 34. In this case, to simplify processing, only those peaks are re-correlated which are determined to have clearly corresponding peaks after checking the preceding and the following peak numbers NO. For example, let us assume that the peak number NO.1 in the previous screen corresponds to the peak number NO.0 in the current screen; the peak number NO.1 in the current screen has no corresponding value (="NO_VALUE"); and the peak number NO.3 in the previous screen corresponds to the peak number NO.2 in the current screen. In this case, the peak number NO.2 in the previous screen is correlated with the peak number NO.1 in the current screen. On the other hand, however, let us assume that the peak number "NO.1" in the previous screen corresponds to the peak number "NO.0" in the current screen; the peak number "NO.1" in the current screen has no corresponding value (="NO_VALUE"); and the peak number "NO.2" in the current screen has no corresponding value (="NO_VALUE"). In that case, the peak number "NO.2" in the previous screen may correspond to the peak number "NO.1" in the current screen, but the peak number "NO.2" in the previous screen may also correspond to the peak number "NO.2" in the current screen depending on the results of the correlation of the peak number "NO.3" in the current screen. Such a case in which the correlation cannot be determined solely by the preceding and the following corresponding peak numbers NO. may result in an incorrect re-correlation and should thus be removed from processing. An outline of this processing is shown in the flowchart of FIGS. 15 and 16.

Figure 15:
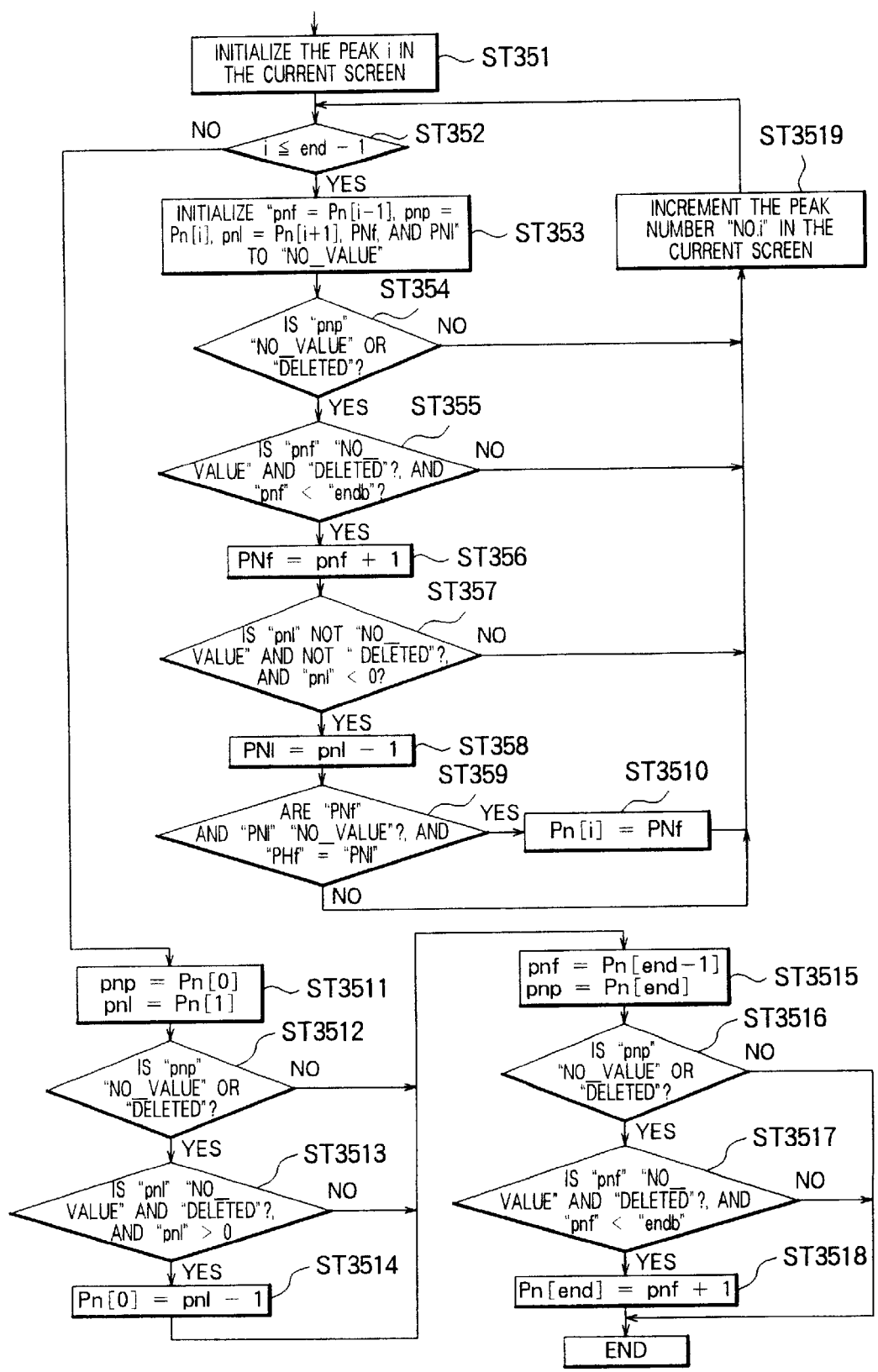
FIG. 15 is a flowchart showing the flow of processing executed by a re-correlation means if there are two or more peaks in the current screen.

FIG. 15 shows the processing executed by the re-correlation means 33 if there are 2 or more peaks in the current screen ("end"≧2). FIG. 16 shows the processing executed by the re-correlation means 35 if there is one peak in the current screen.

As shown in the flowchart in FIG. 15, in those of the peak numbers "NO. i=1 to (end-1)" that have no corresponding peak "Pn[i]"(="NO_VALUE") or that have been deleted (="DELETED"), if there is a peak "Pn[i-1]" corresponding to the peak number "NO.i-1", "Pn[i-1]+1" is determined to be a candidate "PNf" to be re-correlated with the peak number "NO.i", whereas if there is a peak Pn[i+1] corresponding to the peak number "NO. i+1", "Pn[i+1]-1" is determined to be a candidate "PNl" to be re-correlated with the peak number "NO.i". If both "PNf" and "PNl" are present and match, the peak number "NO.i" is correlated so that Pn[i]=PNf(Pnl). If the peak number "NO.i"="0" or "end" and if there is a peak "Pn[1]" or "Pn[end-1]" corresponding to peak number "NO.i=1" or "NO.i=end-1", respectively, "Pn[1]-1" or "Pn[end+1]+1" is determined to be a candidate "PNl" to be re-correlated with the peak number "NO.i=0" or a candidate "PNf" to be re-correlated with the peak number "NO.i= end". In this case, "PNf" and "PNl" must of course be between the peak numbers "NO.0" and "endb".

Figure 16:
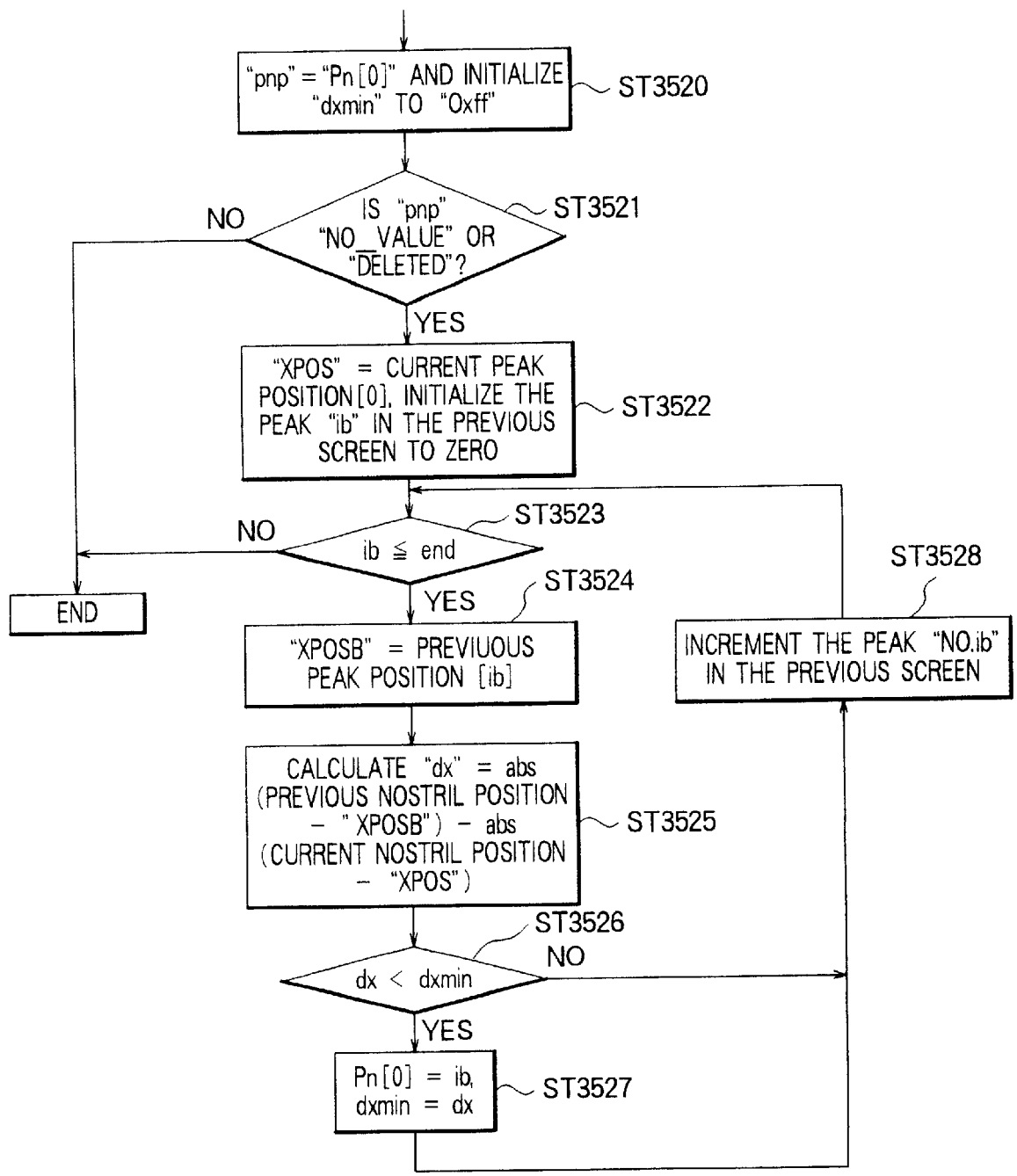
FIG. 16 is a flowchart showing the flow of processing executed by a re-correlation means if there is one peak in the current screen.

As shown in the flowchart of FIG. 16, if the peak Pn[0] corresponding to the peak number "NO.i=0" has no corresponding value (="NO_VALUE") or has been deleted (="DELETED"), the distance "NTOP" between the peak position [0] in the current screen and the x-coordinate position of the nostril in the current screen is compared with the distance "NTOPBib" between the peak positions [0] to ["endb"] in the previous screen and the x-coordinate position of the nostril in the previous screen in order to correlate the corresponding peak Pn[0] with the peak "ib" in the previous screen in which the difference between "NTOP" and "NTOPBib" is smallest.

Based on the results of the correlation, the peak corresponding to the previous image of the eye "13eye" is determined to be a current image of the eye and the peaks corresponding to the previous images of the periphery of the eye "13up" and "13dwn" are determined to be current images of the periphery of the eye in order to update the information on "13eye", "13up", and "13dwn". If, in the current screen, "13eye", "13up", and/or "13dwn" are not found in the corresponding peaks, they are determined to be missing, the information is cleared, and those peaks that can be tracked are tracked. Only the previous information on the evaluation function values, however, is left as a reference value 37. The previous peak position 16$i$ and the middle point 21$ij$ in the direction of Y axis of the entire face element block 20$ij$ are updated each time the screen is changed. Although the area 22$ij$ stored in the memory by the image retrieval means 6 has not been used in this embodiment, it may be used as an index for correlations.

Next, the processing executed by the re-correlation means 35 if there are two or more peaks in the current screen is described with reference to FIG. 15.

First, at step ST351, the process initializes the peak number "NO.i" in the current screen to 1. It is determined at step ST352 whether or not the peak number "NO.i" is smaller than "end-1" (i.e., the loop is repeated for the number of peaks in the current screen -1). If yes, the peak number "NO.pnf =Pn[i-1]" correlated with the peak "i-1", the peak number "NO. pnp=Pn[i]" correlated with the peak i, and the peak number "NO. pnl=Pn[i+1]" correlated with the peak "i+1" are revoked, and "PNf", "PNl" are initialized to "NO_VALUE" (="0xff") at step ST353. Only if "pnp" is "NO_VALUE" (="0xff" set at step ST33) or "DELETED" (="0xdd" set at step ST34), the process proceeds to steps ST355 to ST358, whereas the process proceeds to step ST3519 if "pnp" is not "NO—VALUE" or "DELETED").

During steps ST355 to ST358, the value of "pnp" is estimated from the values of "pnf" and "pnl". Only if "pnf" has a value other than "NO_VALUE" or "DELETED" and smaller than the value "end" at step ST335, "pnf+1" is set in "PNf" at step ST356, and if otherwise, the process transfers to step ST3519. Subsequently, at step ST357, it is determined whether or not "pnl" has a value other than "NO_VALUE" or "DELETED" and larger than zero. If the answer at step ST357 is "yes", "pnl-1" is set in "Pnl", and if otherwise, the process transfers to step ST3519.

Then, if "PNf" and "PNl" are not "NO_VALUE" but match each other at step ST359, "PNf (=PNl)" is set in "Pn[i]" at step ST3510. After the processings at step ST359 and at step ST3510, the peak number "NO.i" in the current screen is incremented at step ST3519 and thereafter the process returns to step ST352. If $i$ becomes larger than "end-1" at step ST352, the process goes to step ST3511.

During steps ST3511 to ST3514, the re-correlation of "i=0" is carried out and during steps ST3515 to ST3518, the re-correlation of "i=end" is carried out. First, "pnp=Pn[0]" and "pnl=Pn[1]" are invoked at step ST3511, and it is determined at step ST3512 whether or not "pnp" is "NO_VALUE" or "DELETED". If "pnp" is not "NO_VALUE" or "DELETED", the process goes to step ST3515, and if otherwise, the process goes to step ST3513 where it is determined whether "pnl" has a value other than "NO_VALUE" and "DELETED" and is larger than zero. If the answer at step ST3513 is "yes", "pnl-1" is set in Pn[0] at step ST3514. If otherwise ("no", i.e., "pnl" is "NO_VALUE" or "DELETED") at step ST3514, the process proceeds to step ST3515.

At step ST3515, "pnf=Pn[end-1]" and "pnp=Pn[end]" are invoked, and at step ST3516 it is determined whether or not pnp is "NO_VALUE" or "DELETED". If not, the process is finished, and if otherwise, the process goes to step ST3517 where it is determined whether or not "pnf" is not "NO_VALUE" and "DELETED" and whether it is smaller than "endb". If the answer at step ST3517 is "yes", then "pnf+1"

is set in "Pn[end]" at step ST3518, whereas if not (i.e., "pnf" is "NO_VALUE" or "DELETED") at step ST3517, the process is finished.

Now, the specific processing executed by the re-correlation means 35 if there is one peak in the current screen will be described with reference to FIG. 16. First, at step ST3520, the peak number "NO.0" is invoked, and the minimum value "dxmin" of the deviation in the distance between the nostril and the eyes in the X direction is initialized to "0xff". Then, the process proceeds to steps ST3522 to ST3528 only if "pnp" is "NO_VALUE" (="0xff"; set at step ST33) or "DELETED" (="0xdd"; set at step ST34) at step ST3521, whereas if otherwise (i.e., "pnp" is not "NO_VALUE" or "DELETED") at step ST3521, the process is finished.

At step ST3522, the position "XPOS" of the peak number "NO.0" in the current screen in the X direction is invoked and the peak number "NO.ib" in the previous screen is initialized to zero. During steps ST3523 to ST3528, the peak corresponding to "Pn[0]" is estimated from the value of the deviation in the distance in direction between the nostril and the eyes. Specifically, it is determined at step ST3523 whether or not "ib" is smaller than "end". If yes, the position "XPOSB" of the peak number "NO. ib" in the previous screen in the X direction is invoked at step ST3524, and the deviation "dx" between the distance between "XPOS" and the current position of the nostril and the distance between "XPOSB" and the previous position of the nostril is calculated at ST3525.

Then, it is determined at step ST3526 whether or not "dx" is smaller than "dxmin", and if yes, the values of "Pn[0]" and "dxmin" are updated at step ST3527, and the peak number "NO.ib" in the previous screen is incremented at step ST3528. If "dx" is larger than "dxmin" at step ST3526, the process goes to step ST3528 while skipping step ST3527. If "ib" becomes larger than "end" at step ST3523, the process is finished.

As can be seen from the above description, during correlation, the image tracking means 7 according to Embodiment 1 can constantly track images of the eyes and their periphery while avoiding erroneous detection or tracking by using duplication elimination and re-correlation, and it can recognize missing images. The image tracking means 7 similarly executes the above processing within the right and the left eye extraction regions.

Figure 17A:
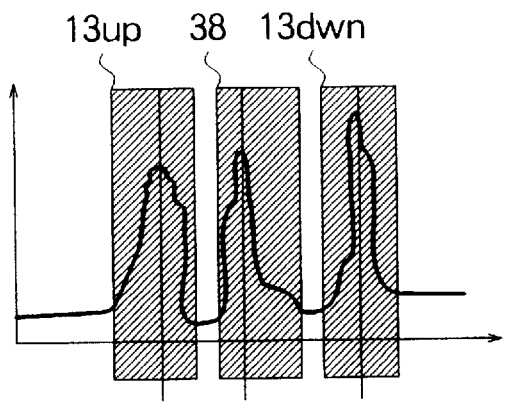
FIGS. 17(a), 17(b) and 17(c) are explanatory views showing different operational states of an image recovery means.
Figure 17B:
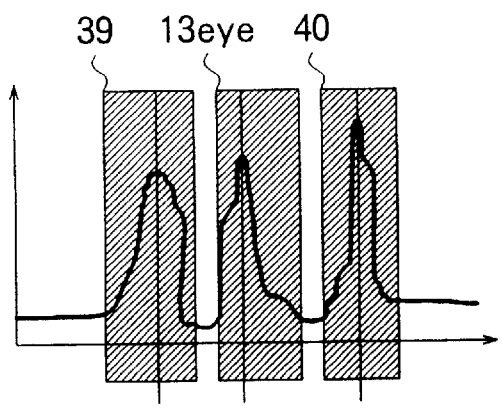
Figure 17C:
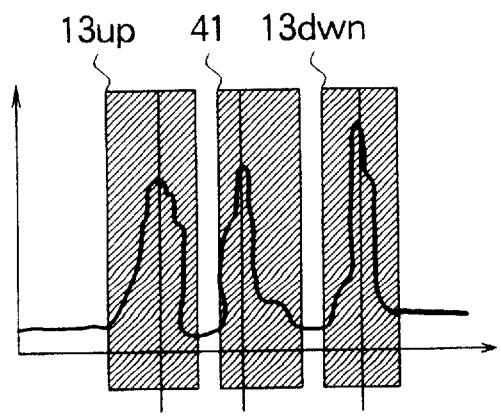

Next, the image recovery means 32 is described. The image recovery means 32 is not required if "13eye", "13up", and "13dwn" are all being tracked. If any of them has been missed and not correlated in the previous screen, there is no corresponding peak in the current screen so in such a situation, the image recovery means 32 is required to recover it. Three cases are possible in which the image recovery means 32 is used. In a first case, "13up" is being tracked. In this case, if a peak 38 that is not "13dwn" is present on the face below "13up", as shown in FIG. 17(*a*), it is determined to be "13eye" unless it is significantly different from the reference value. In a second case, "13eye" is being tracked. In this case, if a peak 39 is present on the face above "13eye", it is determined to be "13up", whereas if a peak 40 is present on the face below "13eye", it is determined to be "13dwn", as shown in FIG. 17(*b*). In a third case, "13dwn" is being tracked. In this case, if a peak 41 that is not "13up" is present on the face above "13dwn", as shown in FIG. 17(*c*), it is determined to be "13eye" unless it is significantly different from the reference value.

The above processing enables accurate re-tracking even during recovery.

Embodiment 2

Figure 18:
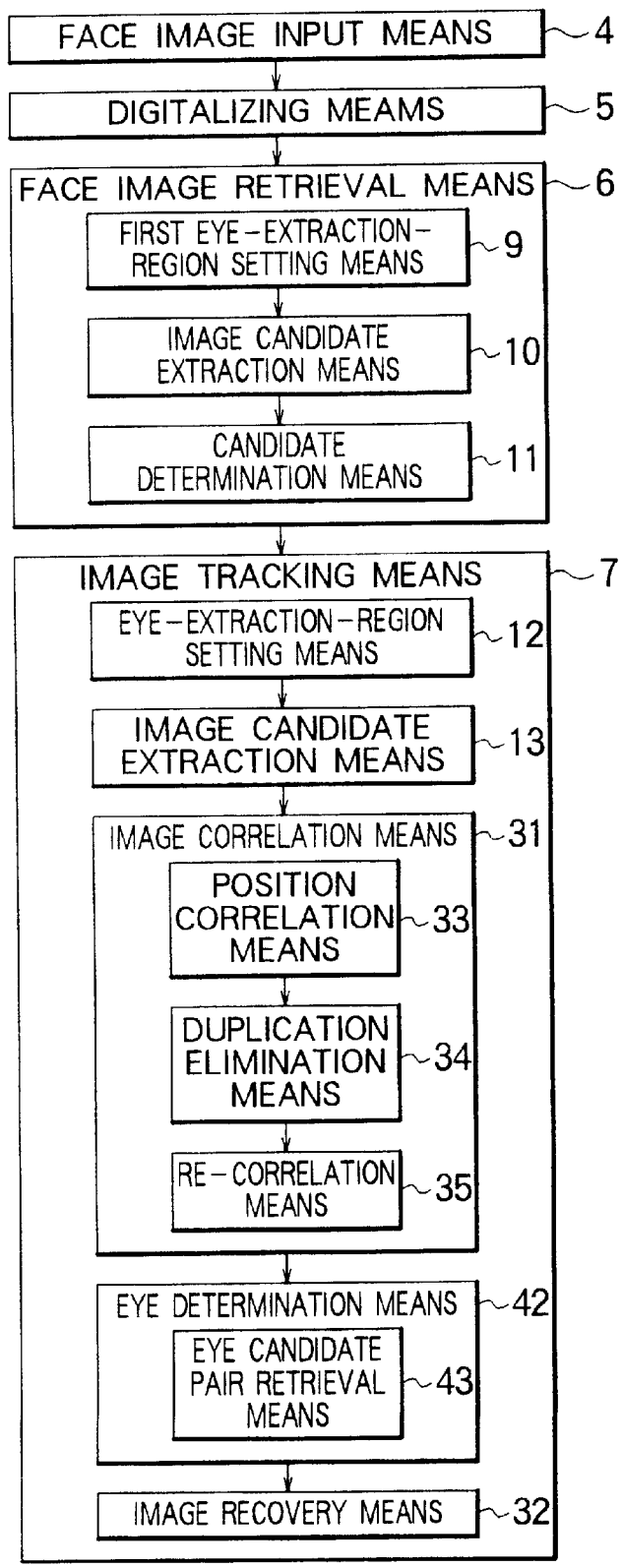
FIG. 18 is a block diagram showing the functional configuration of an eye image tracking apparatus according to a second embodiment (hereinafter simply referred to as Embodiment 2) of this invention.
Figure 19:
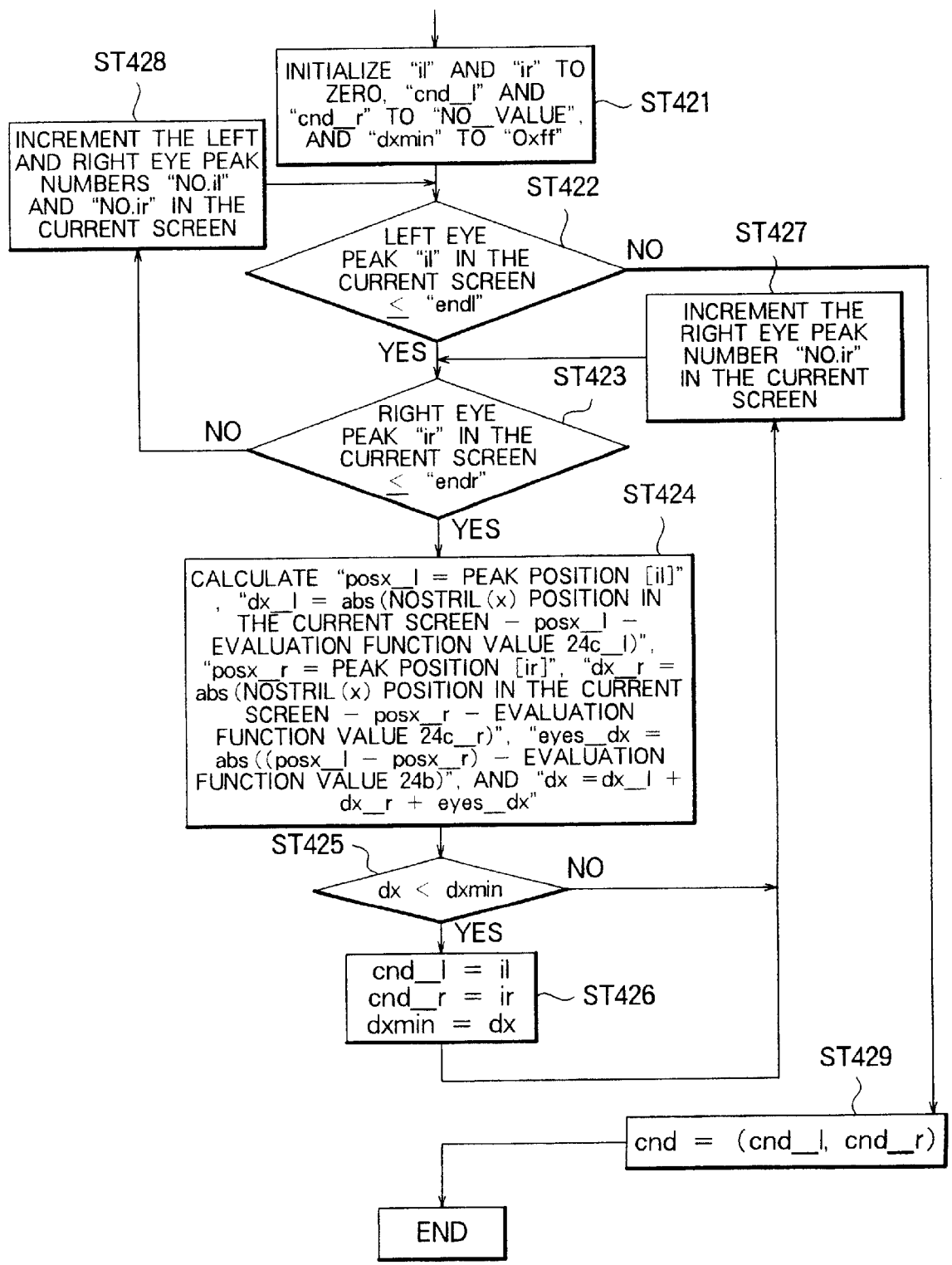
FIG. 19 is a flowchart showing the flow of processing executed by an eye determination means according to Embodiment 2.

FIG. 18 shows the configuration of an eye image tracking apparatus according to Embodiment 2 of this invention. In Embodiment 2, an eye determination means 42 is added to the image tracking means 7 of Embodiment 1, and FIG. 19 shows the processing operation of this embodiment. The image tracking means 7 includes the eye determination means 42 for more accurately tracking an image of the eye based on the results of the correlation executed by the image correlation means 31. The eye determination means 42 includes an eye candidate pair retrieval means 43 for retrieving a pair of the right and the left eyes in order to determine the eyes based on the correlation between the results of the correlation executed by the image correlation means 31 and the eyes retrieved by the eye candidate pair retrieval means 43.

The eye determination means 42 determines one of all the combinations of the right and left peaks in which the relative position relationship between the nostril and the right and left eyes is closest to the previous one, to be an eye candidate pair "43cnd", as shown in FIG. 19.

Next, the operation of Embodiment 2 will be described in detail with reference to FIG. 19. First, at step ST421, the right eye peak number "NO.ir" and left eye peak number "NO.il" are initialized to zero, and "cnd_r" and "cnd_l" in the eye candidate pair ("cnd_r", "cnd_l") are initialized to "NO_VALUE", and the minimum value "dxmin" of the relative deviation is initialized to "0xff". Subsequently, it is determined at step ST422 whether or not the left eye peaks "il" in the current screen are smaller than "endl" (i.e., the loop is repeated for the number of left eye peaks). If yes, then it is determined at step ST423 whether or not the right eye peaks "ir" in the current screen are smaller than "endr" (i.e., the loop is repeated for the number of right eye peaks). If yes, the relative positional deviation "dx" is calculated at step ST424 and it is determined at step ST425 whether or not "dx" is smaller than "dxmin". If yes, the eye candidate pair "cnd_r" and "cnd_l" as well as "dxmin" are updated, and the right eye peak number "NO.ir" in the current screen is incremented at step ST427 (i.e., one of all the combinations of the right and left peaks is selected that has the smallest "dx"). The process then returns to step ST423 from ST427. If "ir" becomes larger than "endr" at step ST423, the process proceeds to step ST428 where the left eye peak number "NO.il" in the current screen is incremented and the right eye peak number "NO.ir" in the current screen is initialized to zero, and then the process returns to step ST422. If "il" becomes larger than "endl" at step ST422, the process goes to step ST429 where cnd ("cnd_r", "cnd_l") are set in the eye candidate pair "cnd", and thereafter the processing is finished.

Here, it is to be noted that the eye candidate pair "43cnd" are compared with the right eye candidate "13eye_r" and left eye candidate "13eye_l" correlated with each other by the image tracking means 7, and the eye candidate is determined based on the results of the comparison. Such determination is made depending on the cases listed below.

Case 1: "13eye_l", "13eye_r", and "43cnd" are all present.
Case 2: Either "13eye_l" or "13eye_r " and "43cnd" are present.
Case 3: Only "43cnd" is present.
Case 4: Only "13eye_l" and "13eye_r " are present.
Case 5: Either "13eye_l" or "13eye_r " is present.

The means for dealing with each of these cases is described below.

In case 1, when both "13eye_r" and "13eye_l" match "43cnd", it can undoubtedly be determine that these are the eyes, and actually such a determination is established. If either of them does not match "43cnd", it is determined that "43cnd" extracted in a pair is the eyes. If neither of them match "43cnd", it is determined that one of the combination and "43cnd" that is closer to the previous combination is the eyes.

In case 2, when "13eye" which is present matches "43cnd", it is determined that "43cnd" extracted in a pair is the eyes. If they do not match, it is determined that one of the combination and "43cnd" that is closer to the previous combination is the eyes. In this case, if if "13eye" is selected, the other eye remains missing.

In case 3, it is determined "43cnd" to be the eyes if there is no problem in the relationship between these eyes and "13up" and "13dwn". Otherwise, the eyes remain missing.

In case 4, it is determined "13eye_r" and "13eye_l" to be the eyes if they meet the pair condition. Otherwise, one of the eyes is selected that has a relative position relationship with respect to the nostril closer to that in the previous image, while maintaining the other eye missing.

In case 5, the relative position relation between "13eye" which is present and the nostril is examined strictly, and it is determined the present "13eye" to be the eye if there is no problem (i.e., the strict position relation is met), while maintaining other eye missing. Otherwise, both eyes remain missing.

The above processing improves the reliability of this invention as compared with the aforementioned Embodiment 1.

Embodiment 3

Figure 20:
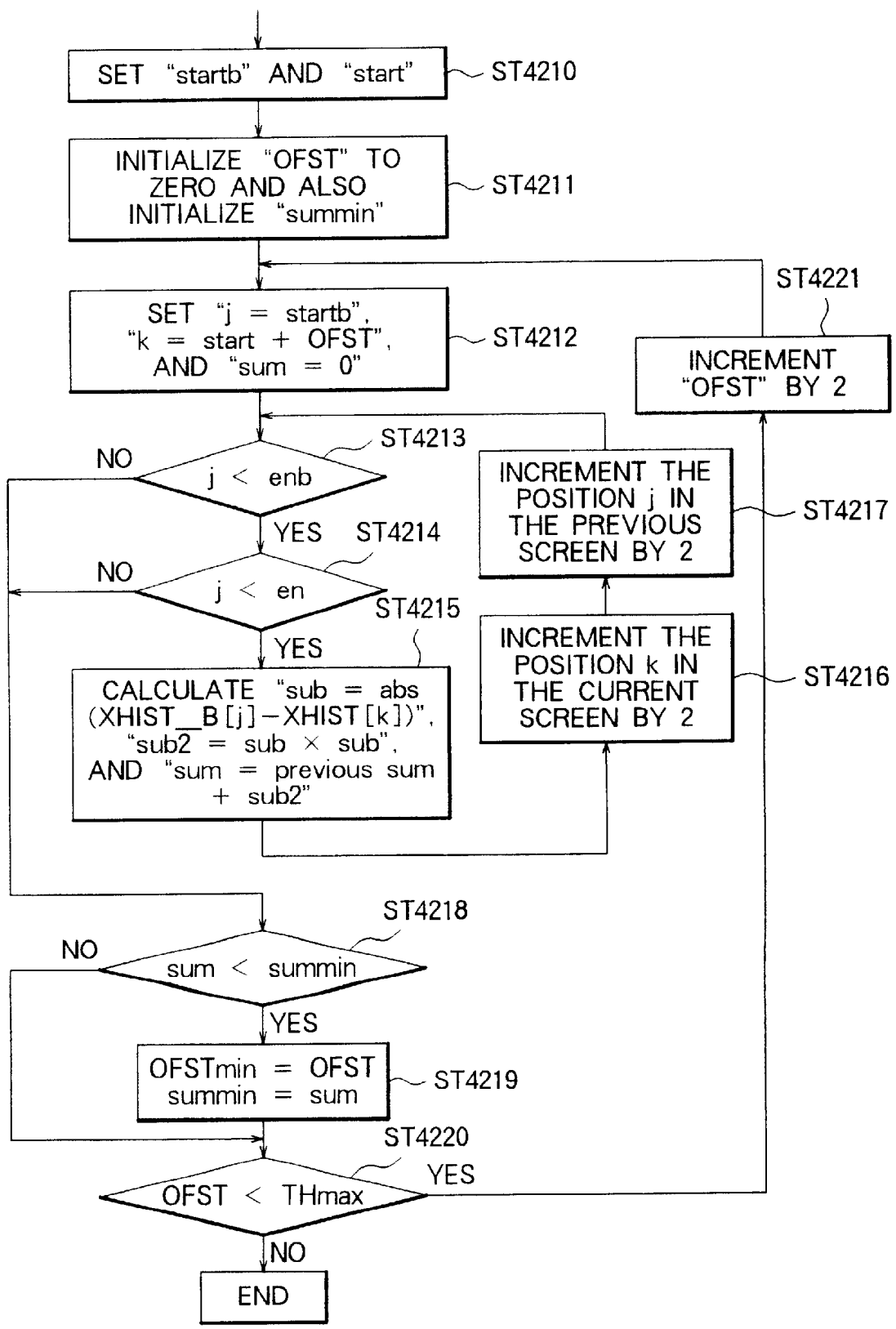
FIG. 20 is a flowchart showing the flow of processing executed by a position correlation means according to a third embodiment (hereinafter simply referred to as Embodiment 3) of this invention.

FIG. 20 is a flowchart showing the operation (processing) of a position correlation means according to Embodiment 3 of this invention. The overall configuration of Embodiment 3 is similar to that of Embodiment 1 or 2. Although the position correlation means 33 in Embodiments 1 and 2 carries out correlations based on information on the positions of the eyes relative to the nostril, Embodiment 3 executes correlations based on information on the positions of the eyes shown in shape histograms within the eye extraction regions.

In Embodiment 3, a relative function is obtained between a current X histogram 15 that projects the sum of the number of pixels in the direction of Y axis at each X coordinate within each of the eye extraction region windows created by the second image candidate extraction means 13 (or the first image candidate extraction means) and a previous X histogram that has been previously similarly created.

In Embodiment 3, the starting and ending positions "st44" and "en45" of each eye extraction region window in the X direction as well as the X histograms created are saved and updated each time the screen is changed.

The processing executed by the position correlation means 33 according to Embodiment 3 is described with reference to FIG. 20.

Figure 21:
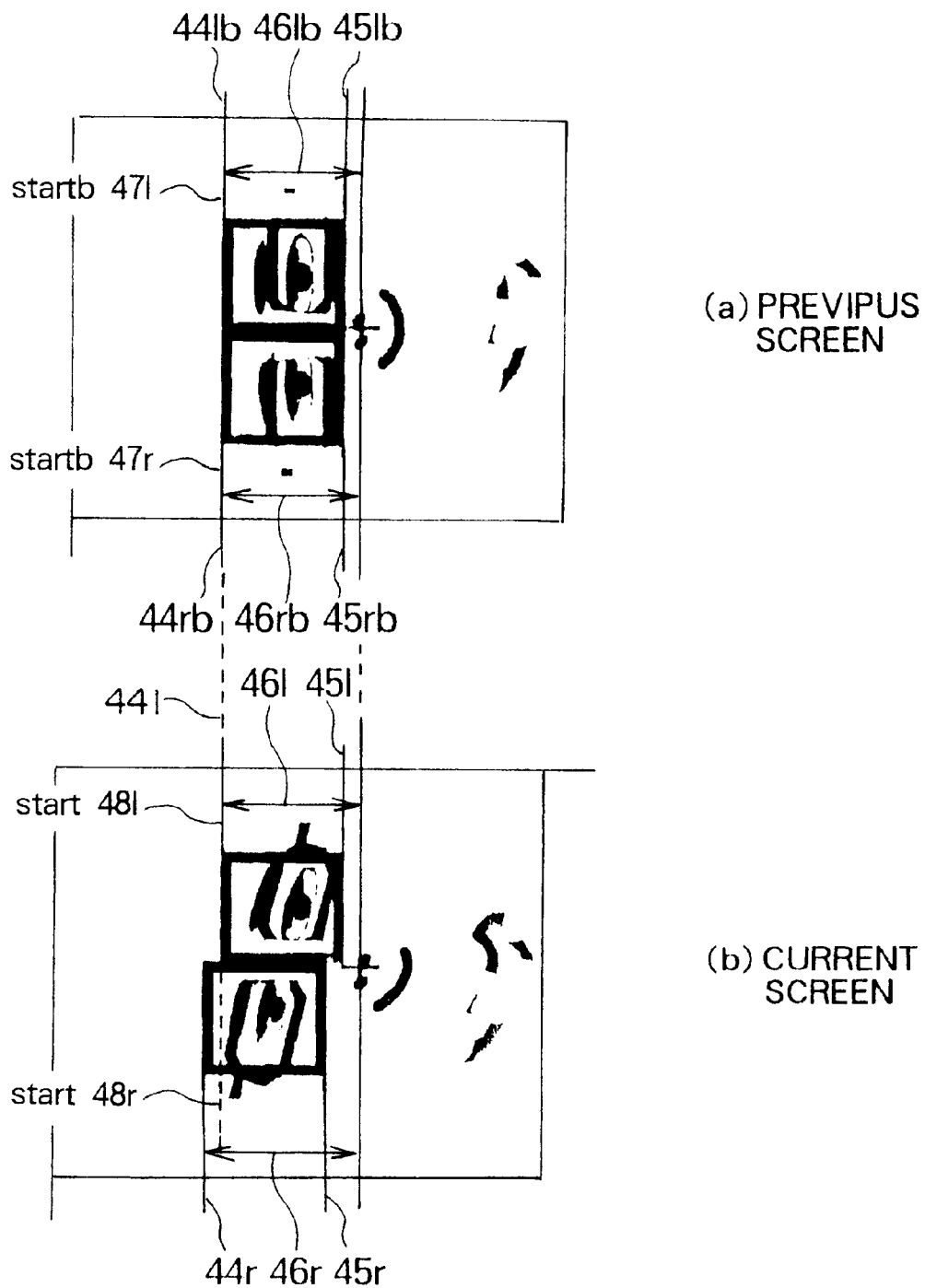
FIG. 21 is an explanatory view of the operation of the position correlation means according to Embodiment 3.
Figure 22:
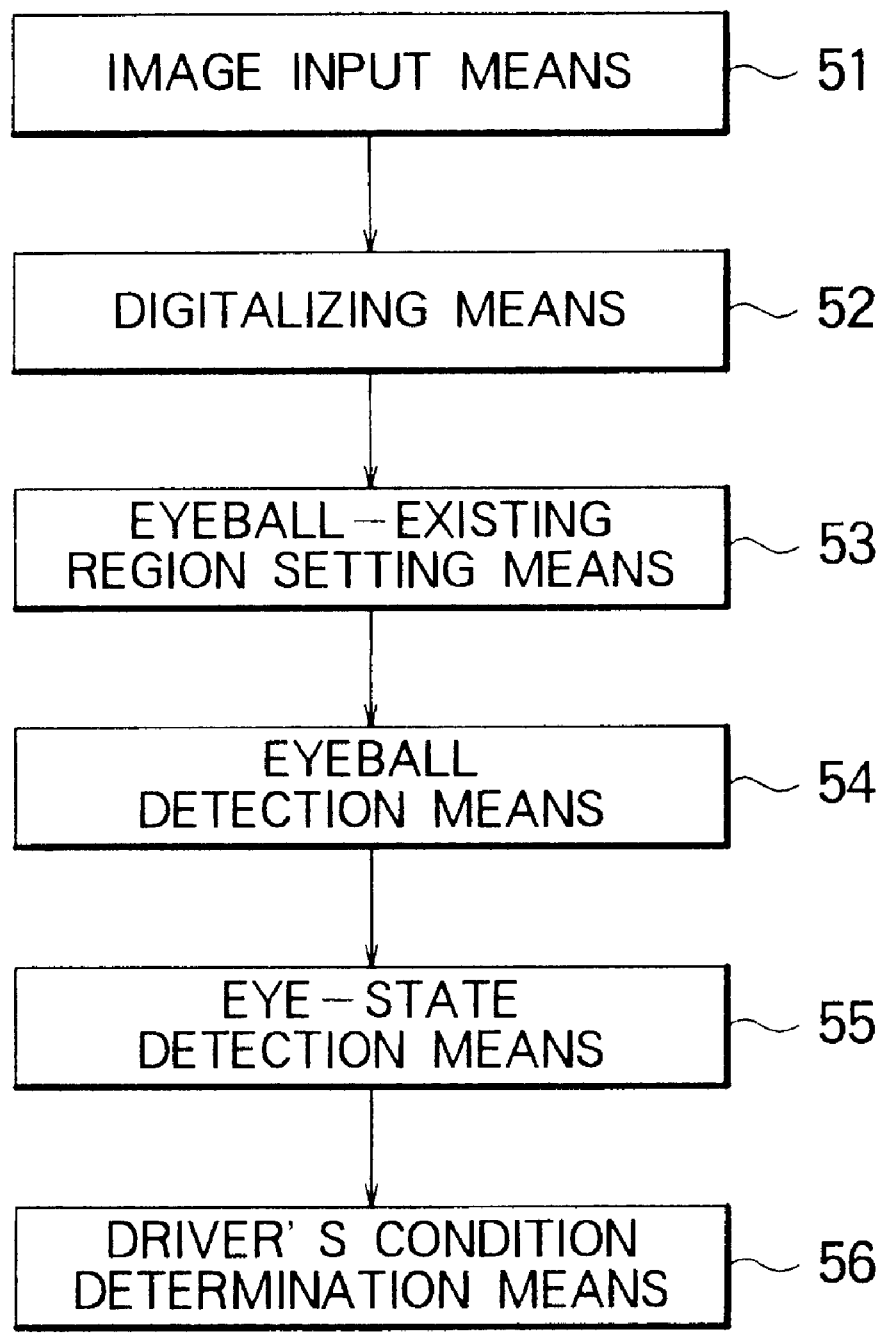
FIG. 22 shows the overall configuration of a conventional eye image tracking apparatus.
Figure 23:
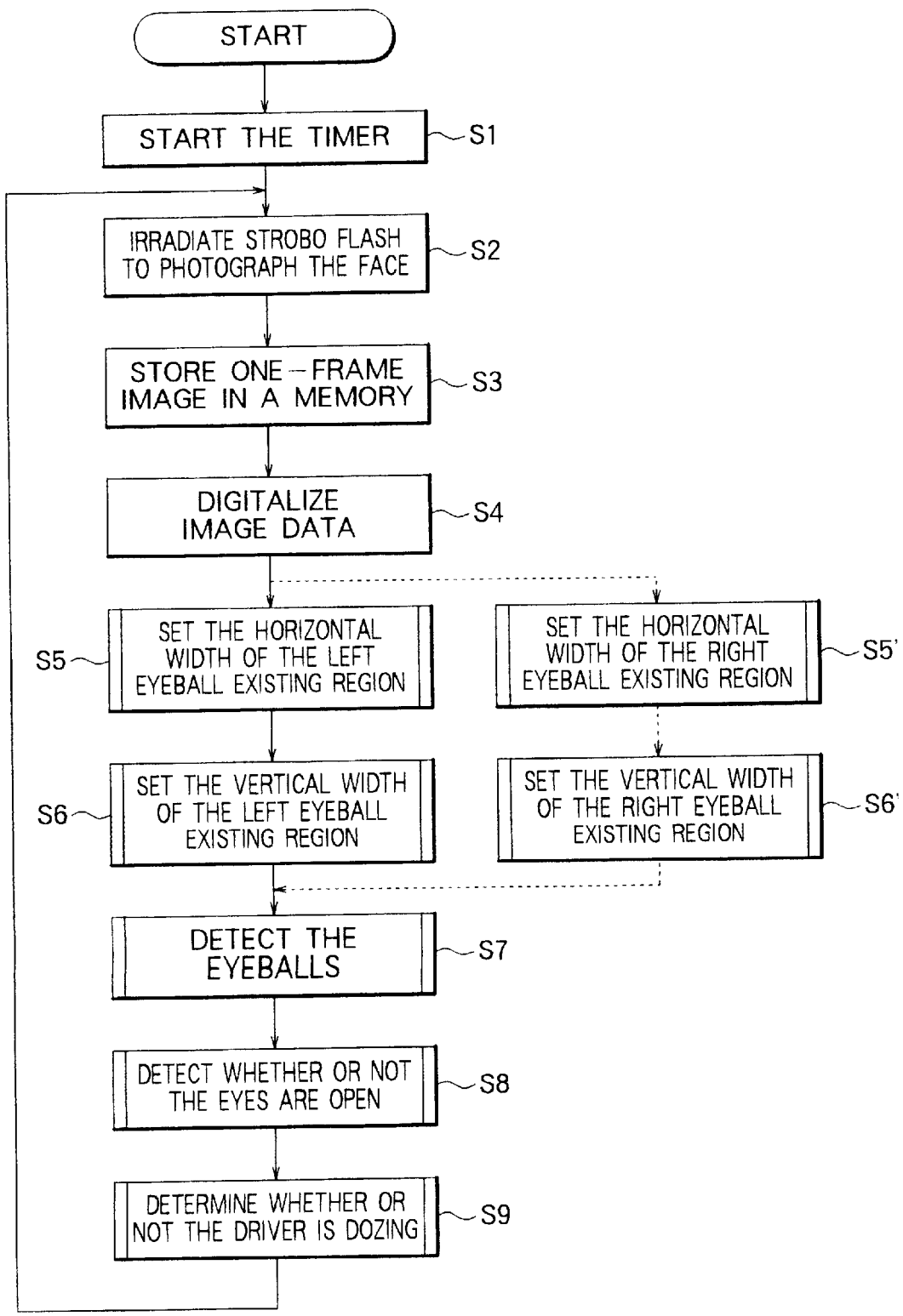
FIG. 23 is a flowchart showing the operation of the conventional apparatus.

As shown in FIG. 21, the position correlation means 33 calculates the distance 46 between the position of the nostril and the window starting point in both the previous and the current screens, and based on the smaller distance, sets scanning starting points "startb47" and "start48" for the previous and the current screen histograms. To facilitate processing, the differential values of the histograms are squared every other pixel starting with the scanning starting point to determine the sum of these values. The processing continues until the histograms in the previous and the current screens have been finished. The same processing is sequentially executed by adding two pixels to the starting point of the current screen as an offset, and a minimum offset "OFSTmin" is determined when the sum is smallest. Accounting for the magnitude of offset within a single screen, the offset has a predetermined maximum value "THmax". Then, since the scanning starting point "startb47" coincides with "start48+OFSTmin", the peak numbers NO. in the previous screen are correlated with the peak numbers NO. in the current screen based on the offset "OFSET50" between the previous and the current screens calculated by the following Equation 49.

$$OFSET50 = startb47 - (start48 + OFSTmin) \qquad \text{Equation 49}$$

Specifically, an array "Pn[i] =ibk" is created as the peak corresponding to one of those peak numbers "NO.ib" in the previous screen (starting number: 0; last number: "endb") that has a peak position within the peak region of the peak numbers "NO.i" in the current screen (starting number: 0; last number: "end") and that has the smallest error "dx" (="Dmin") in the distance between the nostril and the eyes in the X direction, and a corresponding array "Dm[i] =Dmin" of "Dmin" is also created. The position correlation means according to Embodiment 3 has thus been described. As in Embodiment 1, those peaks that have not been correlated are saved in the form of data such as "Pn[i] =NO_VALUE" (="Oxff") indicating that these peaks have no corresponding ones.

Next, the processing of correlation using the matching of the histograms within the eye tracking regions will be described while referring to FIG. 20. First, at step ST4210, a matching starting histogram position is set. A histogram matching starting X-direction position in the previous screen is referred to as "startb", and a histogram matching starting X-direction position in the current screen is referred to as "start", as described above in detail. Then, at step ST4211, the offset of the position of the face "OFST" between the previous screen and the current screen is initialized to zero and also the minimum value of the accumulated squares of histogram errors "summin" is initialized to "Oxff". Then, at step ST4212, the position i of the previous screen is initialized to "startb"; the position k of the current screen is initialized to "start+OFST"; and also the accumulated value "sum" of squares of histogram errors is initialized to zero. It is determined at step ST4213 whether or not i is smaller than "end" (i.e., the end position in the X direction of the eye tracking region in the previous screen). If yes, it is determined at step ST4214 whether or not k is smaller than "en" (i.e., the end position in the X direction of the eye tracking region in the current screen). If yes, the difference "sub" between the X histogram within the eye tracking region of the previous screen "XHIST_B[j]" and the X histogram within the eye tracking region of the current screen "XHIST [k]" is calculated, and then the sum "sum" of the squares of "sub" is calculated. The current and the previous screen positions k and j are incremented by 2 at steps 4216 and 4217, respectively, and the process returns to step ST4213. If the requirements are not met at either step ST4213 or ST4214 (that is, the tracking region in either the previous or the current screen has been finished), the process returns to step ST4218. It is determined at step ST4218 whether or not "sum" is smaller than its minimum value "summin". If yes, the minimum value of "OFST" is initialized to "OFSTmin", and the minimum value "summin" of the accumulated squares of the histogram errors is initialized to "sum", and the process goes to step ST4220. Otherwise, the process proceeds to step ST4220 while skipping step ST4219. It is determined at step ST4220 whether or not "OFST" is smaller than the predetermined maximum threshold "THmax". If yes, "OFST" is incremented by 2 at step ST4221 and the process returns to step ST4212, and if otherwise, the processing is finished.

The above processing improves the reliability in position correlation as compared with Embodiment 1. The subsequent duplication and re-correlation are executed as in Embodiment 1.

As described above, the eye image tracking apparatus according to this invention can track not only an image of the eyes but also images of their periphery to accurately track the image of the eyes without erroneous detection while recognizing the missing of the eyes when the eyes have been missed.

This apparatus can execute the processing at a high speed because the image retrieval means alone determines several evaluation function values to accurately extract the image of the eyes using those values while enabling the image tracking means to extract the image of the eyes through correlation without executing complicated processing. In addition, the image recovery means enables the image of the eyes to be tracked accurately by determining and correcting those images that have been missed and could not be correlated.

Furthermore, the position correlation means allows the processing to be carried out further simply by executing correlation based on information on the positions of the nostril and the eyes.

Furthermore, the position correlation means can reduce the number of correlation operations based on the shape histograms within the eye extraction regions in order to accurately execute correlation without increasing the processing time.

In addition, the duplication elimination, the re-correlation, and the eye determination means can be added or employed to determine and modify erroneous correlations after the initial correlation step, thereby tracking the image of the eyes with further improved accuracy.

What is claimed is:

1. An eye image tracking apparatus comprising:

face image input means for inputting an image of a face;

digitalizing means for digitalizing the input image of the face;

image retrieval means for retrieving images of each of the eyes and its periphery from the digitalized image; and image tracking means for tracking the retrieved images of each eye and its periphery.

2. The eye image tracking apparatus according to claim 1 wherein said image retrieval means comprises:

means for setting a first eye-extraction region for setting an eye extraction region within the digitalized image;

first image candidate extraction means for extracting candidates for the images of one eye and its periphery from said eye extraction region; and candidate determination means for determining the images of the one eye and its periphery from said candidates for the images of the eye and its periphery.

3. The eye image tracking apparatus according to claim 1 wherein said image tracking means comprises:

means for setting a second eye-extraction region for setting an eye extraction region within the digitalized image;

second image candidate extraction means for extracting candidates for the images of the other eye and its periphery from said eye extraction region;

image correlation means for correlating the extracted candidate images with any images in the previous screen; and image recovery means for recovering, as the image candidates, images that appear again after missing.

4. The eye image tracking apparatus according to claim 3 wherein said image tracking means further comprises:

eye determination means for accurately tracking an image of the eyes based on the results of the correlation executed by said image correlation means.

5. The eye image tracking apparatus according to claim 4 wherein said eye determination means comprises:

eye candidate pair retrieval means for retrieving images of a pair of the right and left eyes to determine the eyes based on the correlation between the results of the correlation executed by the image correlation means and the eyes retrieved by the eye candidate pair retrieval means.

6. The eye image tracking apparatus according to claim 3 wherein said image correlation means comprises:

position correlation means for correlating the candidate for the image of the eye extracted by said image candidate extraction means with an image in the previous screen based on information on the position of the eyes relative to the nostril in the previous screen;

duplication elimination means for eliminating the duplication of the correlation; and re-correlation means for correlating any previous image with a candidate that has not been correlated.

7. The eye image tracking apparatus according to claim 3 wherein said image correlation means comprises:

position correlation means for correlating the candidate for the image of the eyes extracted by said image candidate extraction means with any image in the previous screen based on eye position information shown in shape histograms within the eye extraction regions of the previous screen;

duplication elimination means for eliminating the duplication of the correlation; and re-correlation means for correlating any previous image with a candidate that has not been correlated.

* * * * *